United States Patent [19]
Taylor et al.

[11] Patent Number: 6,107,261
[45] Date of Patent: Aug. 22, 2000

[54] COMPOSITIONS CONTAINING A HIGH PERCENT SATURATION CONCENTRATION OF ANTIBACTERIAL AGENT

[75] Inventors: Timothy J. Taylor, Phoenix; Earl P. Seitz, Jr., Scottsdale; Priscilla S. Fox, Phoenix, all of Ariz.

[73] Assignee: The Dial Corporation, Scottsdale, Ariz.

[21] Appl. No.: 09/338,654

[22] Filed: Jun. 23, 1999

[51] Int. Cl.$^7$ .............................. C11D 3/48; C11D 1/83; C11D 3/43

[52] U.S. Cl. ..................... 510/131; 510/130; 510/237; 510/382; 510/386; 510/387; 510/388; 510/432; 510/503; 510/426; 510/427; 510/342

[58] Field of Search ................................. 510/130, 131, 510/237, 382, 386, 387, 388, 432, 503, 426, 427, 342

[56] References Cited

U.S. PATENT DOCUMENTS

| | | | |
|---|---|---|---|
| 4,093,745 | 6/1978 | Wood et al. | 424/358 |
| 4,111,844 | 9/1978 | Polony et al. | 252/106 |
| 4,350,605 | 9/1982 | Hughett | 252/305 |
| 4,518,517 | 5/1985 | Eigen et al. | 252/107 |
| 4,666,615 | 5/1987 | Disch et al. | 252/11 |
| 4,675,178 | 6/1987 | Klein et al. | 424/65 |
| 4,702,916 | 10/1987 | Geria | 424/400 |
| 4,822,602 | 4/1989 | Sabatelli | 424/65 |
| 4,832,861 | 5/1989 | Resch | 252/106 |
| 4,851,214 | 7/1989 | Walters et al. | 424/65 |
| 4,954,281 | 9/1990 | Resch | 252/107 |
| 4,975,218 | 12/1990 | Rosser | 252/117 |
| 5,006,529 | 4/1991 | Resch | 514/721 |
| 5,057,311 | 10/1991 | Kamegai et al. | 424/70 |
| 5,147,574 | 9/1992 | Mac Gilp et al. | 252/108 |
| 5,158,699 | 10/1992 | MacGilp et al. | 252/132 |
| 5,234,618 | 8/1993 | Kamegai et al. | 252/106 |
| 5,415,810 | 5/1995 | Lee et al. | 252/545 |
| 5,417,875 | 5/1995 | Nozaki | 252/106 |
| 5,441,671 | 8/1995 | Cheney et al. | 252/549 |
| 5,462,736 | 10/1995 | Rech et al. | 424/401 |
| 5,480,586 | 1/1996 | Jakubicki et al. | 252/545 |
| 5,635,462 | 6/1997 | Fendler et al. | 510/131 |
| 5,635,469 | 6/1997 | Fowler et al. | 510/406 |
| 5,646,100 | 7/1997 | Haugk et al. | 510/131 |
| 5,653,970 | 8/1997 | Vermeer | 424/70.24 |
| 5,681,802 | 10/1997 | Fujiwara et al. | 510/130 |
| 5,716,626 | 2/1998 | Sakurai et al. | 424/401 |
| 5,730,963 | 3/1998 | Hilliard, Jr. et al. | 424/65 |
| 5,824,650 | 10/1998 | De Lacharriere et al. | 514/15 |
| 5,837,272 | 11/1998 | Fierro, Jr. et al. | 424/401 |
| 5,851,974 | 12/1998 | Sandhu | 510/235 |
| 5,863,524 | 1/1999 | Mason et al. | 424/65 |
| 5,871,718 | 2/1999 | Lucas et al. | 424/65 |
| 5,888,524 | 3/1999 | Cole | 424/402 |

FOREIGN PATENT DOCUMENTS

| | | | |
|---|---|---|---|
| 0 505 935 | 9/1992 | European Pat. Off. | C11D 3/48 |
| WO 95/09605 | 4/1995 | WIPO | A61K 7/50 |
| WO 95/32705 | 12/1995 | WIPO | A61K 7/50 |
| WO 96/06152 | 2/1996 | WIPO | C11D 3/00 |
| WO 97/46218 | 12/1997 | WIPO | A61K 7/48 |
| WO 98/01110 | 1/1998 | WIPO | A61K 7/48 |
| WO 98/55096 | 12/1998 | WIPO | A61K 7/50 |
| WO 98/55097 | 12/1998 | WIPO | A61K 7/50 |

OTHER PUBLICATIONS

Allawala et al., *Journal of the American Pharmaceutical Association*, vol. XLII, No. 5, pp. 267–275 (1953).
Mitchell, *J. Pharm. Pharmacol*, 16, pp. 533–537 (1964).

*Primary Examiner*—Yogendra Gupta
*Assistant Examiner*—Charles I. Boyer
*Attorney, Agent, or Firm*—Marshall, O'Toole, Gerstein, Murray & Borun

[57] ABSTRACT

Antibacterial compositions having enhanced antibacterial effectiveness are disclosed. The antibacterial compositions contain a phenolic antibacterial agent, a surfactant, and water, wherein a percent saturation of the antibacterial agent in a continuous aqueous phase of the composition is at least 50%.

36 Claims, No Drawings

COMPOSITIONS CONTAINING A HIGH PERCENT SATURATION CONCENTRATION OF ANTIBACTERIAL AGENT

FIELD OF THE INVENTION

The present invention is directed to antibacterial compositions, like personal care compositions, having improved antibacterial effectiveness. More particularly, the present invention is directed to antibacterial compositions comprising an antibacterial agent and a surfactant that provide a substantial reduction, e.g., greater than 99%, in Gram positive and Gram negative bacterial populations within one minute.

BACKGROUND OF THE INVENTION

Antibacterial personal care compositions are known in the art. Especially useful are antibacterial cleansing compositions, which typically are used to cleanse the skin and to destroy bacteria and other microorganisms present on the skin, especially the hands, arms, and face of the user.

Antibacterial compositions are used, for example, in the health care industry, food service industry, meat processing industry, and in the private sector by individual consumers. The widespread use of antibacterial compositions indicates the importance consumers place on controlling bacteria and other microorganism populations on skin. It is important, however, that antibacterial compositions provide a substantial and broad spectrum reduction in microorganism populations quickly and without problems associated with toxicity and skin irritation.

In particular, antibacterial cleansing compositions typically contain an active antibacterial agent, a surfactant, and various other ingredients, for example, dyes, fragrances, pH adjusters, thickeners, skin conditioners, and the like, in an aqueous carrier. Several different classes of antibacterial agents have been used in antibacterial cleansing compositions. Examples of antibacterial agents include a bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and triclosan (i.e., 2,4,4'-trichloro-2'-hydroxy-diphenylether). Present-day antimicrobial compositions based on such antibacterial agents exhibit a wide range of antibacterial activity, ranging from low to high, depending on the microorganism to be controlled and the particular antibacterial composition.

Most commercial antibacterial compositions, however, generally offer a low to moderate antibacterial activity. Antibacterial activity is assessed against a broad spectrum of microorganisms, including both Gram positive and Gram negative microorganisms. The log reduction, or alternatively the percent reduction, in bacterial populations provided by the antibacterial composition correlates to antibacterial activity. A log reduction of 3–5 is most preferred, a 1–3 reduction is preferred, whereas a log reduction of less than 1 is least preferred, for a particular contact time, generally ranging from 15 seconds to 5 minutes. Thus, a highly preferred antibacterial composition exhibits a 3–5 log reduction against a broad spectrum of microorganisms in a short contact time. Prior disclosures illustrate attempts to provide such antibacterial compositions, which, to date, do not provide the rapid, broad range control of microorganisms desired by consumers.

It should be noted that high log reductions have been achieved at pH values of 4 and 9, but such log reductions are attributed at least in part to these relatively extreme pH values. Compositions having such pH values can irritate the skin and other surfaces, and, therefore, typically are avoided. It has been difficult to impossible to achieve a high log reduction using an antibacterial composition having a neutral pH of about 5 to about 8, and especially about 6 to about 8.

For example, WO 98/01110 discloses compositions comprising triclosan, surfactants, solvents, chelating agents, thickeners, buffering agents, and water. WO 98/01110 is directed to reducing skin irritation by employing a reduced amount of surfactant.

Fendler et al. U.S. Pat. No. 5,635,462 discloses compositions comprising PCMX and selected surfactants. The compositions disclosed therein are devoid of anionic surfactants and nonionic surfactants.

WO 97/46218 and WO 96/06152 disclose compositions based on triclosan, organic acids or salts, hydrotropes, and hydric solvents.

EP 0 505 935 discloses compositions containing PCMX in combination with nonionic and anionic surfactants, particularly nonionic block copolymer surfactants.

WO 95/32705 discloses a mild surfactant combination that can be combined with antibacterial compounds, like triclosan.

WO 95/09605 discloses antibacterial compositions containing anionic surfactants and alkylpolyglycoside surfactants.

WO 98/55096 discloses antimicrobial wipes having a porous sheet impregnated with an antibacterial composition containing an active antimicrobial agent, an anionic surfactant, an acid, and water, wherein the composition has a pH of about 3.0 to about 6.0.

N. A. Allawala et al., *J. Amer. Pharm. Assoc.—Sci. Ed., Vol. XLII*, no. 5, pp. 267–275, (1953) discusses the antibacterial activity of active antibacterial agents in combination with surfactants.

A. G. Mitchell, *J. Pharm. Pharmacol., Vol.* 16, pp. 533–537, (1964) discloses compositions containing PCMX and a nonionic surfactant that exhibit antibacterial activity. The compositions disclosed in the Mitchell publication exhibit antibacterial activity in at least 47 minutes contact time, thus the compositions are not highly effective.

Prior disclosures have not addressed the issue of which composition ingredient in an antibacterial composition provides bacterial control. Prior compositions also have not provided an effective, fast, and broad spectrum control of bacteria at a neutral pH of about 5 to about 8, and especially at about 6 to about 8.

An efficacious antibacterial composition has been difficult to achieve because of the properties of the antibacterial agents and the effects of a surfactant on an antibacterial agent. For example, several active antibacterial agents, like phenols, have an exceedingly low solubility in water, e.g., triclosan solubility in water is about 5 to 10 ppm (parts per million). The solubility of the antibacterial agent is increased by adding surfactants to the composition. However, an increase in solubility of the antimicrobial agent, and in turn, the amount of antibacterial agent in the composition, does not necessarily lead to an increased antibacterial efficacy.

Without being bound to any particular theory, it is theorized that the addition of a surfactant increases antimicrobial agent solubility, but also typically reduces the availability of the antibacterial agent because a surfactant in water forms micelles above the critical micelle concentration of the surfactant. The critical micelle concentration varies from surfactant to surfactant. The formation of micelles is important because micelles have a lipophilic region that attracts and solubilizes the antibacterial agent, and thereby renders the antibacterial agent unavailable to immediately contact bacteria, and thereby control bacteria in short time period (i.e., one minute or less).

The antibacterial agent solubilized in the surfactant micelles will control bacteria, but in relatively long time frames. The antibacterial agent, if free in the aqueous solution and not tied up in the surfactant micelle (i.e., is activated), is attracted to the lipophilic membrane of the bacteria and performs its function quickly. If the antibacterial agent is tied up in the surfactant micelle (i.e., is not activated), the antibacterial agent is only slowly available and cannot perform its function in a time frame that is practical for cleaning the skin.

In addition, antibacterial agent that is solubilized in the micelle is readily washed from the skin during the rinsing process, and is not available to deposit on the skin to provide a residual antibacterial benefit. Rather, the antibacterial agent is washed away and wasted.

Accordingly, a need exists for an antibacterial composition that is highly efficacious against a broad spectrum of Gram positive and Gram negative bacteria in a short time period, and wherein the antibacterial activity is attributed primarily, or solely, to the presence of the active antibacterial agent in the composition. The present invention is directed to such antibacterial compositions.

SUMMARY OF THE INVENTION

The present invention relates to antibacterial compositions that provide a substantial reduction in Gram positive and Gram negative bacteria in less than about one minute. More particularly, the present invention relates to antimicrobial compositions containing an active antibacterial agent, a surfactant, and water, wherein the antibacterial agent is present in the continuous aqueous phase (in contrast to being present in micelles), in an amount of at least 50% of saturation, when measured at room temperature. The present invention also relates to antimicrobial compositions containing an active antibacterial agent, a surfactant, water, and a hydric solvent and/or a hydrotrope, wherein the antibacterial agent is present in an amount of at least 25% of saturation, when measured at room temperature.

Accordingly, one aspect of the present invention is to provide a liquid, antibacterial composition comprising: (a) about 0.001% to about 10%, by weight, of an antibacterial agent; (b) about 0.1% to about 40%, by weight, of a surfactant selected from the group consisting of a $C_8$–$C_{18}$ alkyl sulfate, a $C_8$–$C_{18}$ fatty acid salt, a $C_8$–$C_{18}$ alkyl ether sulfate having one or two moles of ethoxylation, a $C_8$–$C_{18}$ alkamine oxide, a $C_8$–$C_{18}$ alkyl sarcosinate, a $C_8$–$C_{18}$ sulfoacetate, a $C_8$–$C_{18}$ sulfosuccinate, a $C_8$–$C_{18}$ alkyl diphenyl oxide disulfonate, a $C_8$–$C_{18}$ alkyl carbonate, a $C_8$–$C_{18}$ alpha-olefin sulfonate, a methyl ester sulfonate, and mixtures thereof; and (c) water, wherein the antibacterial agent is present in the composition in an amount of at least 50% of saturation concentration, when measured at room temperature.

Another aspect of the present invention is to provide an alternative embodiment of the antibacterial composition, wherein the composition comprises:

(a) about 0.001% to about 10%, by weight, of an antimicrobial agent;

(b) about 0.1% to about 40%, by weight, of a surfactant selected from the group consisting of an anionic surfactant, a cationic surfactant, a nonionic surfactant, an ampholytic surfactant, and mixtures thereof;

(c) about 0% to about 30%, by weight, of a hydrotrope;

(d) about 0% to about 25%, by weight, of a water-soluble hydric solvent; and (e) water, wherein the composition contains at least one of the hydrotrope and hydric solvent, and wherein the antimicrobial agent is present in the composition in an amount of at least 25% of saturation concentration, when measured at room temperature.

Still another aspect of the present invention is to provide another alternative embodiment of the antibacterial composition, wherein the composition comprises:

(a) 0.001% to about 10%, by weight, of an antimicrobial agent;

(b) 0 to about 10%, by weight, of a surfactant selected from the group consisting of an anionic surfactant, a cationic surfactant, a nonionic surfactant, an ampholytic surfactant, and mixtures thereof;

(c) 0% to about 40%, by weight, of a hydrotrope;

(d) 0% to about 60%, by weight, of a water-soluble hydric solvent; and (e) water, wherein the composition contains at least one of the hydrotrope and hydric solvent in an amount sufficient to solubilize the antimicrobial agent, and wherein the antimicrobial agent is present in the composition in an amount of at least 25% of the saturation concentration, when measured at room temperature.

Yet another aspect of the present invention is to provide an antibacterial composition that exhibits a log reduction against Gram positive bacteria (i.e., S. aureus) of at least 2 after 30 seconds of contact.

Still another aspect of the present invention is to provide an antibacterial composition that exhibits a log reduction against Gram negative bacteria (i.e., E. coli) of at least 2.5 after 30 seconds of contact.

Another aspect of the present invention is to provide an antibacterial composition that exhibits a substantial log reduction against Gram positive and Gram negative bacteria, and has a pH of about 5 to about 8.

Another aspect of the present invention is to provide consumer products based on an antibacterial composition of the present invention, for example, a skin cleanser, a body splash, a surgical scrub, a wound care agent, a hand sanitizer gel, a disinfectant, a mouth wash, a pet shampoo, a hard surface sanitizer, and the like.

A further aspect of the present invention is to provide a method of reducing the Gram positive and/or Gram negative bacteria populations on animal tissue, including human tissue, by contacting the tissue, like the dermis, with a composition of the present invention for a sufficient time, such as about 15 seconds to 5 minutes, to reduce the bacteria level to a desired level.

The above and other novel aspects and advantages of the present invention are illustrated in the following, nonlimiting detailed description of the preferred embodiments.

DETAILED DESCRIPTION OF THE PREFERRED EMBODIMENTS

Personal care products incorporating an active antibacterial agent have been known for many years. Since the introduction of antibacterial personal care products, many claims have been made that such products provide antibacterial properties. However, to be most effective, an antibacterial composition should provide a high log reduction against a broad spectrum of organisms in as short a contact time as possible.

As presently formulated, commercial liquid antibacterial soap compositions provide a poor to marginal time kill efficacy, i.e., rate of killing bacteria. Table 1 summarizes the kill efficacy of commercial products, each of which contains about 0.2% to 0.3%, by weight, triclosan (an antibacterial agent).

TABLE 1

Time Kill Efficacy of Commercial Liquid Hand Soaps

| Product | Organism (Log Reductions after 1 Minute Contact Time) | | |
|---|---|---|---|
| | Gram Positive S. aureus | Gram negative E. coli | Gram negative K. pneum. |
| Commercial Product A | 1.39 | 0.00 | 0.04 |
| Commercial Product B | 2.20 | 0.00 | 0.01 |
| Commercial Product C | 1.85 | 0.00 | 0.00 |

Present day products especially lack efficacy against Gram negative bacteria, such as E. coli, which are of particular concern to human health. The present invention, therefore, is directed to antibacterial compositions having an exceptionally high broad spectrum antibacterial efficacy, as measured by a rapid kill of bacteria (i.e., time kill), which is to be distinguished from persistent kill.

The present antibacterial compositions provide significantly improved time kill efficacy compared to prior compositions. The basis of this improved time kill is the discovery that the antimicrobial efficacy of an active agent can be correlated to the rate at which the agent has access to an active site on the microbe. The driving force that determines the rate of agent transport to the site of action is the difference in chemical potential between the site at which the agent acts and the external aqueous phase. Alternatively stated, the microbicidal activity of an active agent is proportional to its thermodynamic activity in the external phase. Accordingly, thermodynamic activity, as opposed to concentration, is the more important variable with respect to antimicrobial efficacy. As discussed more fully hereafter, thermodynamic activity is conveniently correlated to the percent saturation of the active antibacterial agent in the continuous aqueous phase of the composition.

Many compounds have a solubility limit in aqueous solutions termed the "saturation concentration," which varies with temperature. Above the saturation concentration, the compound precipitates from solution. Percent saturation is the measured concentration in solution divided by the saturation concentration. The concentration of a compound in aqueous solution can be increased over the saturation concentration in water by the addition of compounds like surfactants. Surfactants not only increase the solubility of compounds in the continuous aqueous phase of the composition, but also form micelles, and can solubilize compounds in the micelles.

The % saturation of an active antibacterial agent in any composition, including a surfactant-containing composition, ideally can be expressed as:

$$\% \text{ saturation} = [C/C_S] \times 100\%$$

wherein $C$ is the concentration of antibacterial agent in the composition and $C_S$ is the saturation concentration of the antibacterial agent in the composition at room temperature. While not wishing to be bound by any theory, applicants believe that the continuous aqueous phase of a surfactant-containing composition is in equilibrium with the micellar pseudophase of said composition, and further that any dissolved species, such as an antibacterial active agent, is distributed between the aqueous continuous phase and the micellar pseudophase according to a partition law. Accordingly, the percent saturation, or alternatively the relative thermodynamic activity or relative chemical potential, of an antibacterial active agent dissolved in a surfactant-containing composition is the same everywhere within the composition. Thus, the terms percent saturation of the antibacterial agent "in a composition," "in the aqueous continuous phase of a composition," and "in the micellar pseudophase of a composition" are interchangeable, and are used as such throughout this disclosure.

Maximum antibacterial efficacy is achieved when the difference in thermodynamic activities of the active antibacterial agent between the composition and the target organism is maximized (i.e., when the composition is more "saturated" with the active ingredient). A second factor affecting antibacterial activity is the total amount of available antibacterial agent present in the composition, which can be thought of as the "critical dose." It has been found that the total amount of active agent in the continuous aqueous phase of a composition greatly influences the time in which a desired level of antibacterial efficacy is achieved, given equal thermodynamic activities. Thus, the two key factors affecting the antibacterial efficacy of an active agent in a composition are: (1) its availability, as dictated by its thermodynamic activity, i.e., percent saturation in the continuous phase of a composition, and (2) the total amount of available active agent in the solution.

An important ingredient in antibacterial cleansing compositions is a surfactant, which acts as a solubilizer, cleanser, and foaming agent. Surfactants affect the percent saturation of an antibacterial agent in solution, or more importantly, affect the percent saturation of the active agent in the continuous aqueous phase of the composition. This effect can be explained in the case of a sparingly water-soluble antibacterial agent in an aqueous surfactant solution, where the active agent is distributed between the aqueous (i.e., continuous) phase and the micellar pseudophase. For antibacterial agents of exceedingly low solubility in water, such as triclosan, the distribution is shifted strongly toward the micelles (i.e., a vast majority of the triclosan molecules are present in surfactant micelles, as opposed to the aqueous phase).

The ratio of surfactant to antibacterial agent directly determines the amount of active agent present in the surfactant micelles, which in turn affects the percent saturation of the active agent in the continuous aqueous phase. It has been found that as the surfactant:active agent ratio increases, the number of micelles relative to active molecules also increases, with the micelles being proportionately less saturated with active agent as the ratio increases. Since the active agent in the continuous phase is in equilibrium with active agent in the micellar pseudophase, as the saturation of antibacterial agent in the micellar phase decreases, so does the saturation of the antibacterial agent in the continuous phase. The converse is also true. Active agent solubilized in the micellar pseudophase is not immediately available to contact the microorganisms, and it is the percent saturation of active agent in the continuous aqueous phase that determines the antibacterial activity of the composition. The active agent present in the surfactant micelles, however, can serve as a reservoir of active agent to replenish the continuous aqueous phase as the active agent is depleted.

To summarize, the thermodynamic activity, or percent saturation, of an antibacterial agent in the continuous aqueous phase of a composition drives antibacterial activity. Further, the total amount of available active agent determines the ultimate extent of efficacy. In compositions wherein the active agent is solubilized by a surfactant, the active agent present in surfactant micelles is not directly available for antibacterial activity. For such compositions, the percent saturation of the active agent in the composition, or alternatively the percent saturation of the active agent in the continuous aqueous phase of the composition, determines antibacterial efficacy.

The present compositions are antibacterial compositions having an improved effectiveness against both Gram negative and Gram positive bacteria, and that exhibit a rapid bacteria kill. As illustrated in the following embodiments, an antibacterial composition of the present invention comprises: (a) about 0.001% to about 10%, by weight, of an antibacterial agent; (b) about 0.1% to about 40%, by weight, of a surfactant; (c) an optional hydric solvent; (d) an optional hydrotrope; and (e) water. The compositions have a percent saturation of antibacterial agent in the continuous aqueous phase of at least about 25%, when measured at room temperature. The compositions exhibit a log reduction against Gram positive bacteria of about 2 after 30 seconds contact. The compositions exhibit a log reduction against Gram negative bacteria of about 2.5 after 30 seconds contact.

The following illustrates three important, nonlimiting embodiments of the present invention.

A. Antibacterial Compositions Containing an Antibacterial Agent and a Surfactant In one embodiment of the present invention, the antibacterial compositions comprise an active antibacterial agent, a surfactant, and water. The compositions of embodiment A exhibit a rapid bacteria kill even in the absence of a hydric solvent and a hydrotrope. The presence of a hydric solvent and/or a hydrotrope does not adversely affect the antimicrobial properties of the composition, but such optional ingredients are not necessary ingredients. The compositions can further include additional optional ingredients disclosed hereafter, like pH adjusters, dyes, and perfumes.

1. Antibacterial Agent

An antibacterial agent is present in a composition of the present invention in an amount of about 0.001% to about 10%, and preferably about 0.01% to about 5%, by weight of the composition. To achieve the full advantage of the present invention, the antibacterial agent is present in an amount of about 0.05% to about 2%, by weight, of the composition.

The antibacterial compositions can be ready to use compositions, which typically contain 0.001% to about 2%, preferably 0.01% to about 1.5%, and most preferably about 0.05% to about 1%, of an antibacterial agent, by weight of the composition. The antibacterial compositions also can be formulated as concentrates that are diluted before use with one to about 100 parts water to provide an end use composition. The concentrated compositions typically contain greater than about 0.1% and up to about 10%, by weight, of the antibacterial agent. Applications also are envisioned wherein the end use composition contains greater than 2%, by weight, of the antibacterial agent.

As discussed above, the absolute amount of antibacterial agent present in the composition is not as important as the amount of available antibacterial agent in the composition. The amount of available antibacterial agent in the composition is related to the identity of the surfactant in the composition, the amount of surfactant in the composition, and the presence of optional ingredients in the composition.

To achieve the desired bacteria kill in a short contact time, like 15 to 60 seconds, the continuous aqueous phase of the composition contains an amount of antibacterial agent that is at least about 50%, and preferably at least about 75%, of the saturation concentration of the antibacterial agent in water, when measured at room temperature. To achieve the full advantage of the present invention, the continuous aqueous phase is about 95% to 100% saturated with the antibacterial agent. The amount of antibacterial agent present in the continuous aqueous phase can be defined as the total amount of antibacterial agent in the composition, less any antibacterial agent present in surfactant micelles. The method of determining percent saturation of antibacterial agent in the composition is disclosed hereafter.

The antimicrobial agents useful in the present invention are phenolic compounds exemplified by the following classes of compounds:

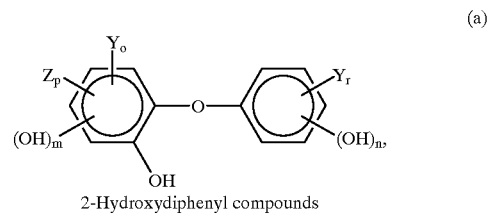

2-Hydroxydiphenyl compounds (a)

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1.

In preferred embodiments, Y is chlorine or bromine, m is 0, n is 0 or 1, o is 1 or 2, r is 1 or 2, and p is 0.

In especially preferred embodiments, Y is chlorine, m is 0, n is 0, o is 1, r is 2, and p is 0.

A particularly useful 2-hydroxydiphenyl compound has the structure:

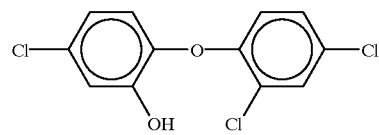

having the adopted name, triclosan, and available commercially under the tradename IRGASAN DP300, from Ciba Specialty Chemicals Corp., Greensboro, N.C. Another useful 2-hydroxydiphenyl compound is 2,2'-dihydroxy-5,5'-dibromo-diphenyl ether.

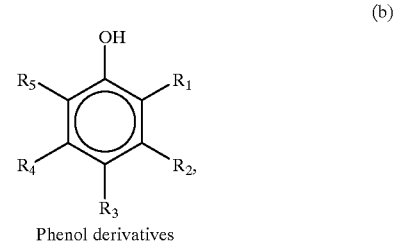

Phenol derivatives (b)

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl, and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in WO 98/55096, incorporated herein by reference.

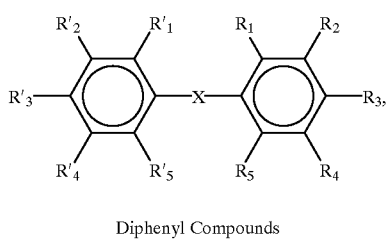

(c)

Diphenyl Compounds wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5', 6,6'-hexachlorodiphenyl sulfide, and 3,3'-dibromo-5,5'-dichloro-2,2'-dihydroxydiphenylamine. Other diphenyl compounds are listed in WO 98/55096, incorporated herein by reference.

2. Surfactant

In addition to the antibacterial agent, a present antimicrobial composition also contains a surfactant. The surfactant is present in an amount of about 0.1% to about 40%, and preferably about 0.3% to about 20%, by weight, of the composition. To achieve the full advantage of the present invention, the antibacterial composition contains about 0.5% to about 15%, by weight, of the surfactant.

Ready-to-use compositions typically contain about 0.1% to about 10%, preferably about 0.3% to about 5%, and most preferably, 0.5% to about 3%, by weight, of the composition. Concentrated compositions suitable for dilution typically contain greater than about 5%, by weight, of a surfactant.

The amount of surfactant present in the composition is related to the amount and identity of the antibacterial agent in the composition and to the identity of the surfactant. The amount of surfactant is determined such that the percent saturation of the antibacterial agent in the continuous aqueous phase of the composition is at least about 50%, preferably at least about 75%, and most preferably at least about 95%.

In this embodiment, wherein the presence of a hydric solvent and a hydrotrope is optional, the identity of the surfactant is important with respect to providing a composition having a percent saturation of antibacterial agent in the continuous aqueous phase of at least about 50%. As illustrated hereafter, surfactants useful in this embodiment of the invention include anionic surfactants and selected cationic surfactants. Nonionic surfactants and anionic surfactants containing a relatively high amount of ethoxylation are not useful in this embodiment. Ethoxylated surfactants containing more than two moles of ethylene oxide have a strong affinity for the antibacterial agent, and in this embodiment substantially reduce the efficacy of the antibacterial agent.

Accordingly, in this embodiment, the surfactant is selected from the following classes of surfactants: $C_8$–$C_{18}$ alkyl sulfate, a $C_8$–$C_{18}$ fatty acid salt, a $C_8$–$C_{18}$ alkyl ether sulfate having one or two moles of ethoxylation, a $C_1$–$C_{18}$ alkamine oxide, a $C_8$–$C_{18}$ alkoyl sarcosinate, a $C_8$–$C_{18}$ sulfoacetate, a $C_8$–$C_{18}$ sulfosuccinate, a $C_8$–$C_{18}$ alkyl diphenyl oxide disulfonate, a $C_8$–$C_{18}$ alkyl carbonate, a $C_8$$C_{18}$ alphaolefin sulfonate, a methyl ester sulfonate, and mixtures thereof. The $C_8$–$C_{18}$ alkyl group contains eight to sixteen carbon atoms, and can be straight chain (e.g., lauryl) or branched (e.g., 2-ethylhexyl). The cation of the anionic surfactant can be an alkali metal (preferably sodium or potassium), ammonium, $C_1$–$C_4$ alkylammonium (mono-, di-, tri), or $C_1$–$C_3$ alkanolammonium (mono-, di-, tri-). Lithium and alkaline earth cations (e.g., magnesium) can be used, but antibacterial efficacy is reduced.

Specific surfactants that can be used in this embodiment include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, cocamine oxide, decylamine oxide, myristamine oxide, ricinoleates, cetyl sulfates, and similar surfactants. Additional examples of surfactants can be found in "CTFA Cosmetic Ingredient Handbook," J. M. Nikitakis, ed., The Cosmetic, Toiletry and Fragrance Association, Inc., Washington, D.C. (1988) (hereafter CTFA Handbook), pages 10–13, 42–46, and 87–94, incorporated herein by reference.

3. Carrier

The carrier in this embodiment comprises water.

4. Optional Ingredients

An antibacterial composition of the present invention also can contain optional ingredients well known to persons skilled in the art. For example, the composition can contain a hydric solvent and/or a hydrotrope. These particular optional ingredients and the amount that can be present in the composition are discussed hereafter.

The compositions also can contain other optional ingredients, such as dyes and fragrances, that are present in a sufficient amount to perform their intended function and do not adversely affect the antibacterial efficacy of the composition. Such optional ingredients typically are present, individually, from 0% to about 5%, by weight, of the composition, and, collectively, from 0% to about 20%, by weight, of the composition.

Classes of optional ingredients include, but are not limited to, dyes, fragrances, pH adjusters, thickeners, viscosity modifiers, buffering agents, foam stabilizers, antioxidants, foam enhancers, chelating agents, opacifiers, and similar classes of optional ingredients known to persons skilled in the art.

Specific classes of optional ingredients include alkanolamides as foam boosters and stabilizers; gums and polymers as thickening agents.; inorganic phosphates, sulfates, and carbonates as buffering agents; EDTA and phosphates as chelating agents; and acids and bases as pH adjusters.

Examples of preferred classes of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

An alkanolamide to provide composition thickening, foam enhancement, and foam stability can be, but are not limited to, cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof.

B. Antibacterial Compositions Containing an Antibacterial Agent, a Surfactant, and a Hydric Solvent and/or a Hydrotrope In another embodiment, the antibacterial compositions comprise an active antibacterial agent, a surfactant, and a hydric solvent and/or a hydrotrope. The compositions of embodiment B exhibit a rapid bacteria kill, and are essentially unlimited in the identity of the surfactant in the composition. The solvent and/or hydrotrope assists in solubilizing the antibacterial agent, and reduces the affinity of the antibacterial agent to enter surfactant micelles. Accordingly, at least 25% saturation of the antibacterial agent in the continuous aqueous phase can be achieved regardless of the identity of the surfactant.

1. Antibacterial Agent

The amount and identity of the antibacterial agent present in this embodiment of the invention is discussed above in A.1.

In addition, to achieve the desired bacteria kill in a short contact time, like 15 to 60 seconds, the continuous aqueous phase of the composition contains an amount of antibacterial agent that is at least about 25%, and preferably at least about 50, and more preferably at least about 75%, of the saturation concentration of the antibacterial agent in water, when measured at room temperature. To achieve the full advantage of the present invention, the continuous aqueous phase is about 95% to 100% saturated with the antibacterial agent.

2. Surfactant

The amount of surfactant present in this embodiment of the present invention is identical to the amount disclosed above in A.2. However, due to the presence of a hydric solvent and/or a hydrotrope, the identity of the surfactant is not limited as in A.2.

In particular, the presence of a hydric solvent and/or hydrotrope, as defined hereafter, reduces the affinity of the antibacterial agent to enter surfactant micelles. Accordingly, a sufficient amount of the antibacterial agent is present in the continuous aqueous phase to quickly and effectively kill a broad spectrum of bacteria regardless of the identity of the surfactant. In embodiments wherein a hydric solvent and hydrotrope are absent, various surfactants, like ethoxylated nonionic surfactants, have such a strong affinity for the antibacterial agent that the antibacterial agent is not available for a rapid bacteria kill.

Accordingly, in this embodiment the surfactant can be an anionic surfactant, a cationic surfactant, a nonionic surfactant, or a compatible mixture of surfactants. The surfactant also can be an ampholytic or amphoteric surfactant, which have anionic or cationic properties depending upon the pH of the composition.

The antibacterial compositions, therefore, can contain an anionic surfactant disclosed above in A.2., and more generally can contain any anionic surfactant having a hydrophobic moiety, such as a carbon chain including about 8 to about 30 carbon atoms, and particularly about 12 to about 20 carbon atoms, and further has a hydrophilic moiety, such as sulfate, sulfonate, carbonate, phosphate, or carboxylate. Often, the hydrophobic carbon chain is etherified, such as with ethylene oxide or propylene oxide, to impart a particular physical property, such as increased water solubility or reduced surface tension to the anionic surfactant.

Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, oxtoxynol or nonoxynol phosphates, taurates, fatty taurides, fatty acid amide polyoxyethylene sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263–266, incorporated herein by reference. Numerous other anionic surfactants, and classes of anionic surfactants, are disclosed in Laughlin et al. U.S. Pat. No. 3,929,678, incorporated herein by reference.

The antibacterial compositions also can contain nonionic surfactants. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$–$C_{18}$) acids, condensation products of ethylene oxide with long chain amines or amides, and mixtures thereof.

Exemplary nonionic surfactants include, but are not limited to, methyl gluceth-10, PEG-20 ethyl glucose distearate, PEG-20 methyl glucose sesquistearate, $C_{11\text{-}15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1–246 and 266–272; in the *CTFA International Cosmetic Ingredient Dictionary, Fourth Ed.,* Cosmetic, Toiletry and Fragrance Association, Washington, D.C. (1991) (hereinafter the CTFA Dictionary) at pages 1–651; and in the *CTFA Handbook,* at pages 86–94, each incorporated herein by reference.

In addition to anionic and nonionic surfactants, cationic, ampholytic, and amphoteric surfactants can be used in the antimicrobial compositions. Cationic surfactants include amine oxides, for example.

Ampholytic surfactants can be broadly described as derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., carboxy, sulfonate, or sulfate. Examples of compounds falling within this description are sodium 3-(dodecylamino)propionate, sodium 3-(dodecylamino)propane-1-sulfonate, sodium 2-(dodecylamino)ethyl sulfate, sodium 2-(dimethylamino) octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

More particularly, one class of ampholytic surfactants include sarcosinates and taurates having the general structural formula

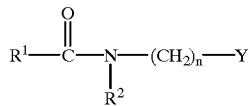

wherein $R^1$ is $C_{11}$ through $C_{21}$ alkyl, $R^2$ is hydrogen or $C_1$–$C_2$ alkyl, Y is $CO_2M$ or $SO_3M$, M is an alkali metal, and n is a number 1 through 3.

Another class of ampholytic surfactants is the amide sulfosuccinates having the structural formula

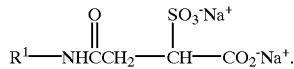

The following classes of ampholytic surfactants also can be used:

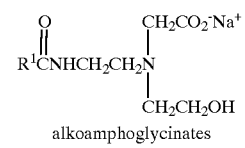
alkoamphoglycinates

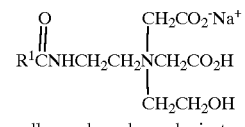
alkoamphocarboxyglycinates

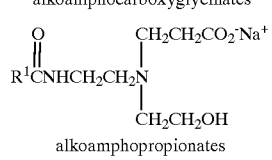
alkoamphopropionates

-continued

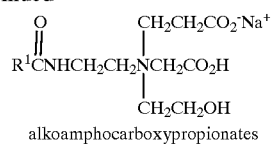
alkoamphocarboxypropionates

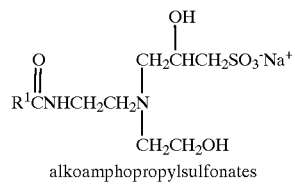
alkoamphopropylsulfonates

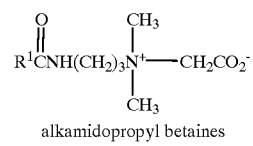
alkamidopropyl betaines

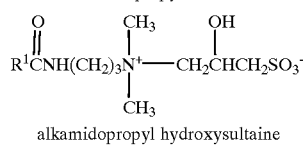
alkamidopropyl hydroxysultaine

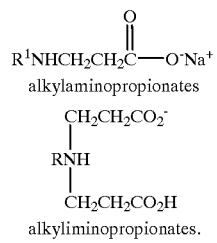
alkylaminopropionates $$\begin{array}{c} CH_2CH_2CO_2^- \\ | \\ RNH \\ | \\ CH_2CH_2CO_2H \end{array}$$
alkyliminopropionates.

Additional classes of ampholytic surfactants include the phosphobetaines and the phosphitaines.

Specific, nonlimiting examples of ampholytic surfactants useful in the present invention are sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, laurylbis-(2-hydroxyethyl) carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, disodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, caprylamphocarboxyglycinate, cocoamphopropionate, cocoamphocarboxypropionate, lauroamphocarboxypropionate, caprylamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

3. Carrier

The carrier in this embodiment comprises water.

4. Optional Ingredients

The optional ingredients discussed in A.4., above, also can be utilized in this embodiment of the invention, in the same amounts and for the same purposes.

5. Hydric Solvent and Hydrotrope

This embodiment of the present invention contains 0% to about 25%, by weight, of a hydric solvent, and 0% to about 30%, by weight, of a hydrotrope, wherein the antibacterial composition contains at least one of the hydric solvent and hydrotrope. Preferred embodiments contain both a hydric solvent and a hydrotrope.

Preferred embodiments contain about 2% to about 20%, by weight, of a hydric solvent and/or about 2% to about 25%, by weight, of a hydrotrope. Most preferred embodiments contain about 5% to about 15%, by weight, of a hydric solvent and/or about 5% to about 20%, by weight, of a hydrotrope.

As defined herein, the term "hydric solvent" is a water-soluble organic compound containing one to six, and typically one to three, hydroxyl groups. The term "hydric solvent" therefore encompasses water-soluble alcohols, diols, triols, and polyols. Specific examples of hydric solvents include, but are not limited to, methanol, ethanol, isopropyl alcohol, n-butanol, n-propyl alcohol, ethylene glycol, propylene glycol, glycerol, diethylene glycol, dipropylene glycol, tripropylene glycol, hexylene glycol, butylene glycol, 1,2,6-hexanetriol, sorbitol, PEG-4, and similar hydroxyl-containing compounds.

A hydrotrope is a compound that has the ability to enhance the water solubility of other compounds. A hydrotrope utilized in the present invention lacks surfactant properties, and typically is a short-chain alkyl aryl sulfonate. Specific examples of hydrotropes includes, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, and disodium succinate.

C. Antibacterial Compositions Containing an Antibacterial Agent and a Hydric Solvent and/or a Hydrotrope In still another embodiment, the antibacterial compositions comprise an active antibacterial agent, and a hydric solvent and/or a hydrotrope. The compositions of embodiment C exhibit a rapid bacteria kill, and also are essentially unlimited in the identity of the surfactant in the composition. The solvent and/or hydrotrope assists in solubilizing the antibacterial agent. Accordingly, at least 25% saturation of the antibacterial agent in the continuous aqueous phase can be achieved even in the absence of a surfactant.

1. Antibacterial Agent

The amount and identity of the antibacterial agent present in this embodiment of the invention is discussed about in A.1.

In addition, similar to embodiment B, in order to achieve the desired bacteria kill in a short contact time, like 15 to 60 seconds, the continuous aqueous phase of the composition contains an amount of antibacterial agent that is at least about 25%, and preferably at least about 50%, and more preferably at least about 75%, of the saturation concentration of the antibacterial agent in water, when measured at room temperature. To achieve the full advantage of the present invention, the continuous aqueous phase is about 95% to 100% saturated with the antibacterial agent.

2. Surfactant

The surfactant is an optional ingredient in this embodiment. However, if present, the amount of surfactant present in this embodiment of the present invention is 0% to about 10% by weight, preferably 0% to about 5%, by weight. To achieve the full advantage of the present invention, the surfactant is present in an amount of 0% to about 2%, by weight. Due to the presence of a hydric solvent and/or a hydrotrope, the identity of the surfactant in this embodiment is identical to the surfactants disclosed in B.2.

3. Carrier

The carrier in this embodiment comprises water.

4. Optional Ingredients

The optional ingredients discussed in A.4., above, also can be utilized in this embodiment of the invention, in the same amounts and for the same purposes.

5. Hydric Solvent and Hydrotrope

The hydric solvent and hydrotrope discussed in B.5., above, also can be utilized in this embodiment of the invention, for the same purpose. However, the amount of hydric solvent and/or hydrotrope present in this embodiment can be greater than the amount disclosed in B.5., above, because an additional amount of solvent and/or hydrotrope may be necessary to solubilize the antibacterial agent in the absence of a surfactant.

Therefore, in embodiment C, the compositions can contain 0% to about 60%, by weight, of a hydric solvent, and 0% to about 40%, by weight, of a hydrotrope. However, the composition contains at least one of the hydrotrope and hydric solvent. Preferred embodiments contain about 2% to about 20%, by weight, of a hydric solvent and/or about 2% to about 25%, by weight, of a hydrotrope. Highly preferred embodiments contain about 5% to about 15%, by weight, of a hydric solvent and/or about 5% to about 20%, by weight, of a hydrotrope. Most preferred embodiments contain both a hydric solvent and a hydrotrope.

In addition, the antibacterial compositions of the present invention do not rely upon a low pH or a high pH to provide a rapid reduction in bacterial populations. Antibacterial compositions of the present invention can have a pH of about 4 to about 9, but at the two extremes of this pH range, the compositions can be irritating to the skin or damaging to other surfaces contacted by the composition. Accordingly, antibacterial compositions of the present invention preferably have a pH of about 5 to about 8, and more preferably about 6 to about 8. To achieve the full advantage of the present invention, the antibacterial compositions have a pH of about 6.5 to about 7.5.

To demonstrate the new and unexpected results provided by the antibacterial compositions of the present invention, the following Examples and Comparative Examples were prepared, and the ability of the compositions to control Gram positive and Gram negative bacteria was determined. The weight percentage listed in each of the following examples represents the actual, or active, weight amount of each ingredient present in the composition. The compositions were prepared by blending the ingredients, as understood by those skilled in the art and as described below.

The following materials were used as ingredients in the examples. The source of each ingredient, and its abbreviation, are summarized below:

a) Alkyl (linear) diphenyl oxide disulfonate, Pilot Chemical Co., Santa Fe Springs, Calif., CALFAX 10L-45 (active=45.4%), b) Alkyl polyglucoside (APG), Henkel Corp., Hoboken, N.J., PLANTAREN 2000N UP (active=55.53%)

c) Alpha-olefin sulfonate (AOS), Stepan Chemical Co., Northfield, Ill., BIOTERGE AS-40 (active=38.80%), d) Ammonium lauryl sulfate (ALS), Henkel Corp., STANDAPOL A (active level=28.3%), e) Ammonium xylene sulfonate (AXS), Stepan Corp., STEPANATE AXS (active=40%), f) Cocamidopropyl betaine (CAPB), McIntyre Group, Ltd., Chicago, Ill., MACKEAM 35-HP (est. 30% active betaine), g) Dipropylene glycol (DPG), Dow Chemical Co., Midland, Mich., h) Disodium laureth sulfosuccinate (DSLScct), McIntyre Group, Ltd., MACKANATE EL (active=33.8%), i) Disodium lauryl sulfosuccinate (DSLrylScct), McIntyre Group, Ltd., MACKANATE LO (active est.=40%), j) DMDM Hydantoin (DMDM), MacIntyre Group, Ltd., MACKSTAT DM (approx. 55% active), k) DowFax Hydrotrope Solution (DFX), Dow Chemical Co., DowFax Hydrotrope Solution (Benzene, 1,1'-oxybis-, sec-hexyl derivatives, sulfonated sodium salt) (active=45.7%), l) Glycerin (GLY), Henkel/Emery, Cincinnati, Ohio, Emery 916 Glycerine (99.7% CP/USP), m) Isopropanol (IPA), Fisher Scientific, Pittsburgh, Pa., 2-Propanol, HPLC Grade A 451-4, n) Lauramine oxide (LAO), McIntyre Group, Ltd., MACKAMINE LO (active=30.55%), o) Liquid Perfume (PF), p) Lithium lauryl sulfate (LLS), Henkel, TEXAPON LLS (active=28.8%), q) Magnesium lauryl sulfate (MLS), Stepan Chemical Co., STEPANOL MG (active=28.3%), r) Methyl ester sulfonate (MES), Stepan Chemical Co., ALPHA-STEP ML-40 (Sodium methyl-2 sulfo laurate and disodium 2-sulfo lauric acid) (active=36.47%), s) Monoethanolamine (MEA), Dow Chemical Co., t) Monoethanolamine lauryl sulfate (MEALS), Albright & Wilson, Cumbria, England, EMPICOL LQ 33/F (active=33%), u) Octylphenol ethoxylate, 9–10 moles EO (TX100), Union Carbide, TRITON-X 100, v) PEG-6ME, polyethylene glycol 300 methyl ether, available from Dow Chemical Co., Midland, Mich., as MPEG 350 (active=est. 100%), w) Poloxymer 338 (F108), BASF, Wyandotte, Mich., PLURONIC F108 (active=est. 100%), x) Potassium cocoate (KCO), McIntyre Group, Ltd., MACKADET 40-K (active=38.4%), y) Potassium laurate (KL), prepared from lauric acid (Sigma, #L-4250, active=99.8%) and potassium hydroxide, z) Potassium oleate (KO), Norman, Fox & Co, Vernon, Calif., NORFOX KO (active=approx. 80%), aa) Propylene glycol (PG), Dow Chemical Co., USP Grade (active level=99.96%), bb) Sodium 2-ethylhexyl sulfate (S2EHS), Henkel, SULFOTEX OA (active=39.68%), cc) Sodium $C_{12}$–$C_{18}$ sulfate (SC12-18S), Henkel, TEXAPON ZHC needles (active=90.95%), dd) Sodium cocoamphoacetate (SCA), McIntyre Group, Ltd., MACKAM IC-90 (active=approx. 32%), ee) Sodium cumene sulfonate (SCS), Stepan Chemical Co., STEPANATE SCS (active=44.6%), ff) Sodium decyl sulfate (SDecS), Henkel, SULFOTEX 110 (active=30.80%), gg) Sodium lauroyl sarcosinate (SLSarc), Hampshire Chemical Co., Lexington, Mass., HAMPOSYL L-30 Type 724 (active=29.9%), hh) Sodium lauryl ether sulfate, 1 mole EO (SLES-1), Henkel, STANDAPOL ES-1 (active=25.40%), ii) Sodium lauryl ether sulfate, 2 mole EO (SLES-2), Henkel, STANDAPOL ES-2 (active level=25.71%), jj) Sodium lauryl sulfate/sodium dodecyl sulfate (SLS/SDS), BDH Biochemical, BDH Ltd., Poole, England, (active=99.0%), kk) Sodium lauryl sulfoacetate (SLSA), Stepan Chemical Co., LANTHANOL LAL (active=72.65%), ll) Sodium octyl sulfate (SOS), Henkel, STANDAPOL LF (active=32.90%), mm) Sodium salt of NEODOX 23-4 (NDX23-4), Shell Chemical Co., derived from NEODOX 23-4, a compound having a 194 molecular weight chain, 4 moles of EO and a carboxylate group (active=94.2%), nn) Sodium tridecyl sulfate (SC13S), Rhodia, Parsippany, N.J., RHODAPON TDS (active=24.65%), oo) Sodium xylene sulfonate (SXS), Stepan Chemical Co., STEPANATE SXS (active level=40-42%), pp) Triclosan (TCS), IRGASAN DP-300, Ciba Specialty Chemicals Corp., Greensboro, N.C. (GC assay on lots used=99.8–99.9% active TCS; mp=56.0–58.0 C.), qq) Triethanolamine lauryl sulfate (TEALS), Henkel, STANDAPOL T (active=40.1%), rr) Tripropylene Glycol (TPG), Dow Chemical Co., Tripropylene Glycol, ss) Water—Unless otherwise indicated, the water was prepared as follows: deionized (DI) water was distilled once through a Corning AG-3 water still.

The following methods were used in the preparation and testing of the examples:

a) Determination of Rapid Germicidal (Time Kill) Activity of Antibacterial Products. The activity of antibacterial compositions was measured by the time kill method, whereby the survival of challenged organisms exposed to an antibacterial test composition is determined as a function of time. In this test, a diluted aliquot of the composition is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated.

In general, the time kill method is known to those skilled in the art.

The composition can be tested at any concentration from 0–100%. The choice of which concentration to use is at the discretion of the investigator, and suitable concentrations are readily determined by those skilled in the art. For example, termined by those skilled in the art. For example, viscous samples usually are tested at 50% dilution, whereas nonviscous samples are not diluted. The test sample is placed in a sterile 250 ml beaker equipped with a magnetic stirring bar and the sample volume is brought to 100 ml, if needed, with sterile deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about 108 colony forming units per ml (cfu/ml).

The table below lists the test bacterial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| Staphylococcus aureus | 6538 | S. aureus |
| Escherichia coli | 11229 | E. coli |
| Klebsiella pneumoniae | 10031 | K. pneum. |
| Salmonella choleraesuis | 10708 | S. choler. |

S. aureus is a Gram positive bacteria, whereas E. coli, K. pneum, and S. choler. are Gram negative bacteria.

The beaker containing the test composition is placed in a water bath (if constant temperature is desired), or placed on a magnetic stirrer (if ambient laboratory temperature is desired). The sample then is inoculated with 1.0 ml of the test bacteria suspension. The inoculum is stirred with the test composition for the predetermined contact time. When the contact time expires, 1.0 ml of the test composition/bacteria mixture is transferred into 9.0 ml of Tryptone-Histidine-Tween Neutralizer Solution (THT). Decimal dilutions to a countable range then are made. The dilutions can differ for different organisms. Plate selected dilutions in triplicate on TSA+ plates (TSA+ is Trypticase Soy Agar with Lecithin and Polysorbate 80). The plates then are incubated for 25±2 hours, and the colonies are counted for the number of survivors and the calculation of percent or log reduction. The control count (numbers control) is determined by conducting the procedure as described above with the exception that THT is used in place of the test composition. The plate counts are converted to cfu/ml for the numbers control and samples, respectively, by standard microbiological methods.

The log reduction is calculated using the formula

Log reduction=$\log_{10}$ (numbers control)−$\log_{10}$(test sample survivors).

The following table correlates percent reduction in bacteria population to log reduction:

| % Reduction | Log Reduction |
|---|---|
| 90 | 1 |
| 99 | 2 |
| 99.9 | 3 |
| 99.99 | 4 |
| 99.999 | 5 | b) Preparation of saturated solutions of TCS in water: A four liter flask was equipped with a 3-inch magnetic stir bar and charged with approximately 7.5 grams (g) TCS and 3 liters (L) of water. The flask then was placed in a water bath, stirred, and heated (40–45° C.) for at least 8 hours. The flask containing the resulting TCS/water suspension was removed from the water bath, and the warm suspension filtered through a Coors #32-H porcelain Buchner funnel equipped with Whatman #40 (5.5 cm) filter paper. The filtering assembly was attached to a two liter vacuum filter flask, and filtration was conducted in batches. The filtrate then was transferred to another four liter flask and allowed to cool. Typically, fine needles of TCS crystals formed after the filtrate was stored at room temperature for a few days.

For some time kill studies, the TCS solution was refiltered at room temperature before use in the study. For other time kill studies, a small amount of crystalline TCS was allowed to remain in the test container to ensure saturation in the event of a temperature change. It was assumed that TCS crystals present in the time kill test vessel would not affect test results because crystalline TCS is unavailable to act on the bacteria (i.e., is not solubilized).

To determine the concentration of TCS in the water solutions, filtered samples (in triplicate) were analyzed by HPLC. The apparatus used to filter the solutions was a Whatman AUTOVIAL®, with 0.45 μm PTFE membrane and glass microfiber prefilter, cat. No. AV125UORG. TCS concentrations were calculated using a linear regression line fit (Microsoft EXCEL® software) to TCS/IPA standards included on the same HPLC run.

c) Preparation of aqueous TCS/surfactant compositions: A French square bottle was charged with a solution containing a variable concentration of a surfactant and 0.3%, by weight, TCS. The mixture was stirred and heated (35–40° C.) for several hours until the TCS was solubilized. Variable transformer-controlled heat lamps were used for warming and the temperature of the solution was monitored with a digital thermometer. Stirring then was stopped, TCS seed crystals (about 1 mg) were added to the solution, and the mixture was allowed to stand at about 20° C. In a few days, crystals were observed on the bottom of solution containers in which the maximum solubility of TCS was exceeded.

The approximate concentration of surfactant necessary to almost completely solubilize the 0.3% TCS was determined by use of an experimental design in which the concentration of surfactant was serially reduced by a factor of two over a series of test samples until the approximate saturation point of TCS in the surfactant was observed. Then the difference in concentration (saturated vs. just solubilized) was halved until a close endpoint for TCS saturation could be determined. The saturation point of TCS/surfactant compositions could be effectively estimated with small-scale (15 to 100 mL) samples, but about 600–800 g samples were required to obtain reliable final results. The initial ranges, therefore, were established with small-scale samples, and the final concentrations were determined using larger-scale samples.

d) Preparation of compositions containing TCS and a solvent or solvent/hydrotrope combination: TCS first was dissolved in the solvent used in the composition. Water then was added to the TCS/solvent composition, followed by the addition of about 1 mg of TCS seed crystals, and the resulting mixture was allowed to stand at about 20° C. to crystallize. In compositions containing a solvent, hydrotrope, and surfactant, the TCS was dissolved in the solvent as above, and then the hydrotrope and surfactant were added to the TCS/solvent solution. The resulting mixture then was diluted to the batch total with water. Adjustment of pH also was performed, if required. The mixture was stirred at room temperature for about an hour, seed TCS was added, and the mixture allowed to stand and crystallize as above. The determination of the TCS saturation point described above also was used (i.e., halving surfactant concentrations). Methods similar to the above for determination of maximum additive concentration have been described in the literature. For example, P. H. Elworthy et al., "Solubilization by surface-active agents and its application in chemistry and biological sciences," Chapman and Hall, Ltd., London, pp. 62–65 (1968), describes determination of concentrations near saturation by observing turbidity of the mixture. A similar technique was used by observing the sample at right angles with a high-intensity light from a small flashlight equipped with a beam focusing attachment (i.e., MINI MAGLITE® AA, MAG Instruments, California, USA). This method also was used with solutions very near to saturation to enhance observation of small amounts of crystals formed on the bottom of containers.

Table 2 summarizes the results of time kill tests performed on TCS/water compositions. Two series of results, I and II, demonstrate the effect of % saturation in TCS/water compositions, i.e., that within a given test series, reduction in % saturation produces a concomitant reduction in time kill efficacy.

TABLE 3-continued

TCS in Solvent and/or Hydrotrope Systems

| TCS (ppm) | Solvent/ Hydrotrope | S. aureus | | E. coli | |
|---|---|---|---|---|---|
| | | sec. | 1 min. | sec. | 1 min. |
| 0 | 5% SXS | | 0.33 | | −0.15 |
| 57 | 5% SCS | | 3.64 | | 0.80 |
| 0 | 5% SCS | | −0.05 | | −0.11 |
| 448 | 20% PG/10% SXS | >4.14/30 | >4.14 | >5.25/30 | >5.25 |

TABLE 2

Time Kill Results for Saturated TCS/Water Compositions

| | | TCS | LOG REDUCTION | | | | | | |
|---|---|---|---|---|---|---|---|---|---|
| | | (g/mL) | S. aureus | | E. coli | | K. pneum. | | S. chol. |
| | Sample | (by HPLC) | 1 min/or t | 5 min. | 1 min/or t | 5 min | 1 min/or t | 5 min | 1 min/or t | 5 min |
| I | 100% sat'd. | 9.3 × 10⁻⁷ | 1.07/15s | >3.91 | 0.44/15s | >4.06 | 0.32/15s | >4.00 | | |
| | 50% sat'd. | 3.9 × 10⁻⁷ | 0.03/15s | 1.71 | 0.13/15s | 1.15 | 0.21/15s | 2.76 | | |
| | 10% sat'd. | 6.7 × 10⁻⁸ | 0.03/15s | 0.02 | 0.06/15s | 0.08 | 0/15s | 0.14 | | |
| II | 100% sat'd. | 9.6 × 10⁻⁶ | 3.93 | | 1.76 | | 2.85 | | 2.15 | |
| | 50% sat'd. | 4.9 × 10⁻⁶ | 0.24 | | 0.26 | | 0.35 | | 1.28 | |

Comparing the data in Tables 2 and 3 shows that at the very lowest concentration of TCS (i.e., 5 to 10 ppm), the efficacy of time kill is reduced compared to samples containing higher levels of TCS. For example, a sample in Table 2 containing 0.93 ppm TCS has a log reduction of 0.44 after 15 seconds vs. *E. coli*, whereas a sample in Table 3 containing 484 ppm TCS had a log reduction of 4.13 after 15 seconds vs. the same organism. This effect is more apparent at shorter-contact time periods. Another example, in more complex compositions is illustrated in samples in Table 3, i.e., 50 ppm TCS (est.)/10%PG/5%SXS vs. (448 ppm TCS (est.)/20%PG/10%SXS). The sample with the higher TCS concentration showed at least a log improvement in bacterial reduction after 1 minute. The data in Table 3 also show differences in efficacy when different solvents/hydrotropes are used with approximately the same TCS concentrations.

TABLE 3

TCS in Solvent and/or Hydrotrope Systems

| TCS (ppm) | Solvent/ Hydrotrope | S. aureus | | E. coli | |
|---|---|---|---|---|---|
| | | sec. | 1 min. | sec. | 1 min. |
| 112 (est) | 17% IPA | | >4.42 | | >3.56 |
| 0 | 17% IPA | | 0.42 | | −0.24 |
| 110 (est) | 23.85% PG | | >4.39 | | 2.37 |
| 342 | 40.01% PG | 4.97¹⁾/30²⁾ | >5.17 | 4.29/30 | >4.67 |
| 484 | 41.86% PG | >3.46/15 | >3.46 | 4.13/15 | >4.38 |
| 510 | 42.53% PG | >5.17/30 | >5.17 | 4.47/30 | >4.67 |
| 723 | 44.20% PG | >3.46/15 | >3.46 | >4.38/15 | >4.38 |
| 603 | 45.05% PG | >4.69/15 | >4.69 | 4.21/15 | >4.65 |
| 895 | 47.52% PG | >5.17/30 | >5.17 | 4.42/30 | >4.67 |
| 1385 | 50.00% PG | >4.49/15 | >4.49 | 4.45/15 | >4.65 |
| 0 | 50.00% PG | 0.15/15 | 0.13 | 0.25/15 | 0.26 |
| 0 | 75.00% PG | 1.20/15 | 2.35 | 0.35/15 | 1.73 |
| 63 | 5% SXS | | >4.43 | | 0.96 |

TABLE 3-continued

TCS in Solvent and/or Hydrotrope Systems

| TCS (ppm) | Solvent/ Hydrotrope | S. aureus | | E. coli | |
|---|---|---|---|---|---|
| | | sec. | 1 min. | sec. | 1 min. |
| 0 | 20% PG/10% SXS | 0.05/30 | 0.05 | 1.16/30 | 1.35 |
| 50 (est) | 10% PG/5% SXS | | 3.42 | | 3.18 |
| 0 | 10% PG/5% SXS | | 0.05 | | 0.35 |
| 50 (est) | 10% PG/5% SCS | | 0.59 | | 4.96 |
| 0 | 10% PG/5% SCS | | −0.03 | | 0.96 |
| 502 (est) | 14.5% DPG/10% SXS | >3.63/30 | >3.63 | >4.44/30 | >4.44 |
| 0 | 14.5% DPG/10% SXS | 0.03.30 | 0.04 | 0.26/30 | 0.17 |
| 112 (est) | 17% IPA | | >4.11 | | >3.79 |
| 0 | 17% IPA | | 0.89 | | 1.23 |
| 110 (est) | 23.85% PG | | | | |
| 342 | 40.01% PG | 4.33/30 | 5.29 | 2.52/30 | 3.51 |
| 484 | 41.86% PG | 2.96/15 | >3.44 | 1.14/15 | 2.31 |
| 510 | 42.53% PG | 4.61/30 | >5.64 | 1.56/30 | 2.27 |
| 723 | 44.20% PG | >3.44/15 | >3.44 | 1.29/15 | 2.59 |
| 603 | 45.05% PG | 2.60/15 | 4.79 | 1.79/15 | >4.50 |
| 895 | 47.52% PG | 5.26/30 | >5.64 | 2.92/30 | 4.33 |
| 1385 | 50.00% PG | 3.26/15 | >5.04 | 2.69/15 | >4.59 |
| 0 | 50.00% PG | 0.54/15 | 0.63 | 0.17/15 | 0.24 |
| 0 | 75.00% PG | 1.98/15 | >3.44 | 1.34/15 | 3.56 |
| 63 | 5% SXS | | | | |
| 0 | 5% SXS | | | | |
| 57 | 5% SCS | | | | |
| 0 | 5% SCS | | | | |
| 448 (est) | 20% PG/10% SXS | >4.32/30 | >4.32 | 3.17/30 | >3.68 |
| 0 | 20% PG/10% SXS | 0.22/30 | 0.37 | 0.25/30 | 1.29 |
| 50 (est) | 10% PG/5% SXS | | | | |
| 0 | 10% PG/5% SXS | | | | |

TABLE 3-continued

TCS in Solvent and/or Hydrotrope Systems

|  |  | S. aureus | | E. coli | |
|---|---|---|---|---|---|
| TCS (ppm) | Solvent/ Hydrotrope | sec. | 1 min. | sec. | 1 min. |
| 50 (est) | 10% PG/5% SCS | | | | |
| 0 | 10% PG/5% SCS | | | | |
| 502 (est) | 14.5% DPG/10% SXS | >4.14/30 | >4.14 | >4.14/30 | >4.14 |
| 0 | 14.5% DPG/10% SXS | 0.34/30 | 0.39 | 0.36/30 | 0.47 |

[1] log reduction; and
[2] seconds.

The compositions of the present invention contain a surfactant, which potentially can reduce the efficacy of the antibacterial agent. The following examples show the unexpected benefits achieved by compositions of the present invention.

EXAMPLE 1

In this example, a composition of the present invention was compared to three commercially available antibacterial cleansing compositions in a time kill test using a contact time of 5 minutes. A composition of the present invention (Product A) was a saturated solution containing 0.3% triclosan in a 1.5% aqueous sodium lauryl sulfate (SLS). The three commercially available antibacterial compositions having unknown triclosan concentrations, were Jergens Antibacterial (JA) Hand Soap, a product of Andrew Jergens Inc.; Clean and Smooth (CS), a product of Benckiser; and Soft Soap (SSp), a product of Colgate Palmolive.

| | | | Log Reduction at 5 minutes (time kill) | | | |
|---|---|---|---|---|---|---|
| Product | Triclosan (%) | % Saturation[3] | S. aureus | E. coli | K. pneum. | S. chol. |
| A | 0.3 | 100 | >4.47 | >4.41 | >4.36 | 4.67 |
| JA | Unk. | Unk. | 2.48 | 0.20 | 0.18 | — |
| Cs | Unk. | Unk. | 2.80 | 0.00 | 0.10 | — |
| SSp | Unk. | Unk. | 1.62 | 0.00 | 0.20 | — |

[1] "—" means not tested;
[2] "Unk." means Unknown; and
[3] "% saturation" means percent saturation of TCS in the continuous aqueous phase.

Example 1 demonstrates the surprising improvement in log reduction of bacteria populations provided by an inventive composition compared to currently available commercial antibacterial compositions. Thus, an aqueous composition containing triclosan in SLS, at 100% saturation, offers significantly greater antibacterial efficacy than any of the three commercial products tested, against Gram positive and against Gram negative microorganisms, both of which can present a significant health threat to consumers.

EXAMPLE 2

This example demonstrates that the antibacterial activity of an inventive composition is attributable to the active antibacterial agent, as opposed to the surfactant. Test compositions A-1 and A-2 were prepared. Composition A-1 is a solution containing 0.3% triclosan, 1.35% ammonium lauryl sulfate, with the balance being water. Composition A-1 is 100% saturated with triclosan. Composition A-2 is a "placebo," i.e., an aqueous 1.35% ammonium lauryl sulfate solution that is free of the active antibacterial agent.

| | | | Log Reduction at 5 minutes (time kill) | | | |
|---|---|---|---|---|---|---|
| Product | Triclosan % | % Saturation | S. aureus | E. coli | K. pneum. | S. chol. |
| A-1 | 0.30 | 100 | >3.61 | 3.16 | >4.39 | 3.73 |
| A-2 | 0 | 0 | >3.61 | 0.25 | 0.15 | 0.04 |

The inventive composition A-1 clearly provided an excellent, broad spectrum antibacterial activity, whereas the "placebo" composition A-2 exhibited an extremely limited spectrum of activity. Composition A-2 has especially poor efficacy against Gram negative organisms. Control of Gram negative organisms is of particular concern to consumers because such organisms present a significant health threat. The excellent broad spectrum activity of composition A-1 clearly shows that the antibacterial activity is unambiguously attributed to the presence of the antibacterial agent in the continuous aqueous phase.

EXAMPLE 3

In this example, a solvent, (i.e., propylene glycol (PG)) was used to solubilize triclosan in an aqueous carrier. No hydrotrope or surfactant was present. Composition A-3 contained 0.0872% by weight triclosan, 47.5% aqueous PG, and the balance being water. Composition A-3 was 100% saturated with triclosan and is a composition of the present invention. Test composition A-4 was a "placebo" consisting of 47.5% PG, by weight, and the balance water. This example illustrates an added advantage of including an optional hydric solvent in the composition. In particular, it was observed that the excellent broad spectrum activity illustrated in earlier examples at contact times of 1 and 5 minutes can be achieved in the presence of the hydric solvent at a contact time of 30 seconds. This example further demonstrates that the antibacterial activity of a present composition is unambiguously attributable to the presence of the antibacterial agent.

| | | | Log Reduction at 30 seconds (time kill) | | | |
|---|---|---|---|---|---|---|
| Product | Triclosan % | % Saturation | S. aureus | E. coli | K. pneum. | S. chol. |
| A-3 | 0.0872 | 100 | >5.17 | 4.42 | 5.26 | 2.92 |
| A-4 | 0.0 | 0 | 0.15 | 0.25 | 0.54 | 0.17 |

EXAMPLE 4

This example illustrates the effect of the identity of the surfactant on the antibacterial activity of the composition. The test results summarized below were performed on a wide variety of compositions containing either an anionic surfactant or representative cationic, anionic/nonionic, amphoteric, and nonionic surfactants. The percent saturation of TCS in the compositions of this example is at least about 90%.

| Surfactant Type | Active Conc. | Surfactant and Amount | S. aureus (1 min) | E. coli (1 min) |
|---|---|---|---|---|
| Anionic | 0.3% TCS | 1.6% Sodium Lauryl Sulfate (SLS) | ++++ | ++++ |
| Anionic | 0.3% TCS | 1.35% Ammonium Lauryl Sulfate (ALS) | ++++ | +++ |
| Anionic | 0.3% TCS | 1.5% Triethanolamine Lauryl Sulfate (TEALS) | +++ | ++++ |
| Anionic | 0.3% TCS | 5% Sodium Octyl Sulfate (SOS) | ++++ | ++++ |
| Anionic | 0.3% TCS | 9.5% Sodium 2-Ethylhexyl Sulfate (S2EHS) | ++++ | ++++ |
| Cationic | 0.3% TCS | 1.5% Lauramine Oxide (LAO) | ++++ | ++++ |
| Anionic | 0.3% TCS | 2.5% Sodium Decyl Sulfate (SdecS) | ++++ | + |
| Anionic | 0.3% TCS | 2.5% Sodium Tridecyl sulfate (SC13S) | ++++ | 0 |
| Anionic | 0.3% TCS | 1.5% Lithium Lauryl Sulfate (LLS) | ++++ | 0 |
| Anionic | 0.3% TCS | 1.5% Potassium Cocoate (KCO) | ++++ | + |
| Anionic | 0.3% TCS | 2.0% Methyl Ester Sulfonate (MES) | ++++ | 0 |
| Anionic | 0.3% TCS | 1.25% Sodium Lauroyl Sarcosinate (SLSarc) | ++++ | 0 |
| Anionic | 0.3% TCS | 1% Sodium Lauryl Sulfoacetate (SLSA) | +++ | 0 |
| Anionic | 0.3% TCS | 3% C10 (Linear) Sodium Diphenyl Oxide Disulfonate (L10-45) | ++++ | 0 |
| Anionic | 0.3% TCS | 1.5% Disodium Lauryl Sulfosuccinate (DSLrylScet) | +++ | 0 |
| Anionic/Nonionic | 0.3% TCS | 1.25% Sodium Lauryl Ether Sulfate, 1-mole EO (SLES-1) | ++++ | 0 |
| Anionic/Nonionic | 0.3% TCS | 1% Sodium Lauryl Ether Sulfate, 2-mole EO (SLES-2) | ++++ | 0 |
| Amphoteric | 0.3% TCS | 1.25% Sodium Cocoamphoacetate (SCA) | 0 | 0 |
| Amphoteric | 0.3% TCS | 1.75% Cocamidopropyl Betaine (CAPB) | 0 | 0 |
| Anionic | 0.3% TCS | 1.25% Alpha-Olefin Sulfonate (AOS) | n/a | 0 |
| Anionic | 0.3% TCS | 1.5% Sodium Alkyl Sulfate, $C_{12-18}$ (SC12-185) | ++ | 0 |
| Anionic | 0.3% TCS | 1.5% Magnesium Lauryl Sulfate (MLS) | n/a | 0 |
| Anionic/Nonionic | 0.3% TCS | 2.0% Sodium Myreth-4 Carboxylate (NaNDX23-4) | 0 | 0 |
| Anionic/Nonionic | 0.3% TCS | 1.25% Disodium Laureth Sulfosuccinate (DSLSect) | ++ | 0 |
| Nonionic | 0.3% TCS | 2.5% Alkyl Polyglucose (APG) | 0 | 0 |
| Nonionic | 0.3% TCS | 4% Octoxynol-9 (TX100) | 0 | 0 |

Key: log reduction in time kill test
++++ >3.99
+++ >2.99
++ >1.99
+ >0.99
0 <0.99

The results summarized above demonstrate, unexpectedly, that antibacterial agents and anionic surfactants form highly effective antibacterial compositions when the % saturation of antibacterial agent in the composition is high, i.e., at least 50%. In addition, it was observed that, within a homologous series of surfactants, efficacy can vary (i.e., in the sodium alkyl sulfate homologous series, sodium lauryl sulfate and sodium octyl sulfate yielded high efficacy formulas). The efficacy with respect to the cation also is unexpected (i.e., sodium, ammonium, and triethanolammonium lauryl sulfates provided high efficacy formulas, whereas lithium and magnesium lauryl sulfates did not).

EXAMPLE 5

The following table summarizes the effect of surfactant identity on the antibacterial activity of the composition. This example expands upon the data provided in Example 4. The table includes results of tests performed on a wide variety of compositions containing either anionic surfactants or representative examples containing cationic, anionic/nonionic, amphoteric, and nonionic surfactants.

The results demonstrate that various anionic surfactants form highly effective systems. The surfactants associated with very high activity (i.e., a high log reduction for both Gram positive (S. aureus) and Gram negative (E. coli) bacteria) include sodium lauryl sulfate, sodium octyl sulfate, sodium 2-ethylhexyl sulfate and lauramine oxide.

However, it is possible that the high activity of the lauramine oxide containing composition was due primarily to the surfactant.

Series I (Lauryl Sulfates) demonstrates efficacy effects attributed to the cation. The sodium lauryl sulfate had the highest efficacy, wherein ammonium, monoethanolammonium and triethanolammonium exhibited intermediate efficacy. Lithium and magnesium sulfates exhibited low efficacy. Potassium lauryl sulfate was not tested because of its low solubility at room temperature.

Comparing Series I (Lauryl Sulfates) and Series II (Other Alkyl Sulfates) shows that efficacy varies within a homologous series (i.e., sodium n-alkyl sulfates). Sodium lauryl sulfate and sodium octyl sulfate yield high efficacy formulas, as does the branched chain surfactant, sodium 2-ethylhexyl sulfate.

The data in Series III (Alkyl Carboxylates) suggests that TCS/carboxylate compositions are not highly active against Gram negative bacteria, but are of acceptable activity against Gram positive bacteria.

The results for Series IV (EO-Containing Surfactants) confirm observations that ethylene oxide (EO) in surfactants tends to inactivate TCS. The activity of SLES-1 and SLES-2 vs. *S. aureus* is attributed to the anionic ("lauryl sulfate-like" character) of these anionic/nonionic surfactants.

The results for Series V (Miscellaneous Surfactants) shows that these compositions exhibit moderate to low activity, with the exception of lauramine oxide. The portion of high activity of LAO is attributed to the surfactant alone because of its quasi-cationic character. The remaining surfactant/TCS compositions in Series V showed varied activity vs. *S. aureus* (Gram positive) and very little activity vs. *E. coli* (Gram negative).

| | | | | |
|---|---|---|---|---|
| | | TCS in Simple Surfactant Systems | | |
| Type | Active Conc. | Other Ingredients | *S. aureus* (30s/1 min.) | *E. coli* (30s/1 min.) |
| | | Series I--Lauryl Sulfates | | |
| Anionic | 0.3% TCS | 1.6% sodium lauryl sulfate (SLS) | >3.94/>3.94 | 4.36/4.36 |
| | 0% TCS | 1.6% sodium lauryl sulfate (SLS) | >3.94/>3.94 | 1.51/2.96 |
| Anionic | 0.3% TCS | 1.35% ammonium lauryl sulfate (ALS) | >3.97/>3.97 | 1.39/3.95 |
| | 0% TCS | 1.35% ammonium lauryl sulfate (ALS) | >3.97/>3.97 | −0.07/−0.02 |
| Anionic | 0.3% TCS | 1.5% monoethanolamine lauryl sulfate (MEALS) | 2.29/4.03 | 0.58/2.04 |
| Anionic | 0.3% TCS | 1.5% triethanolamine lauryl sulfate (TEALS) | 2.74/3.73 | 1.3/4.38 |
| Anionic | 0.3% TCS | 1.5% lithium lauryl sulfate (LLS) | —/4.1 | .51/.81 |
| Anionic | 0.3% TCS | 1.5% magnesium lauryl sulfate (MLS) | —/— | 0.45/0.52 |
| | | Series II--Other Alkyl Sulfates | | |
| Anionic | 0.3% TCS | 5% sodium octyl sulfate (SOS) | >4.39/>4.39 | >4.83/>4.83 |
| | 0% TCS | 5% sodium octyl sulfate (SOS) | 1.76/1.81 | >4.47/>4.47 |
| Anionic | 0.3% TCS | 9.5% sodium 2-ethylhexyl sulfate (S2EHS) | >4.34/>4.84 | >4.47/>4.47 |
| | 0% TCS | 9.5% sodium 2-ethylhexyl suifate (S2EHS) | >3.39/>3.39 | >4.45/4.35 |
| Anionic | 0.3% TCS | 2.5% sodium decyl sulfate (Sdeds) | >4.39/>4.39 | 0.59/1.23 |
| Anionic | 0.3% TCS | 2.5% sodium tridecyl sulfate (SC135) | 3.24/>3.39 | −0.04/0.31 |
| Anionic | 0.3%TCS | 1.5% sodium alkyl sulfate C12-18 (SC12-18S) | 2.09/2.85 | 0.06/0.01 |
| | | Series III--Alkyl Carboxylates | | |
| Anionic | 0.3% TCS | 1.5% potassium cocoate (KCO) | >4.34/>4.34 | 0.35/1.73 |
| Anionic | 0.3% TCS | 1.0% potassium oleate (KO) | 0.55/0.83 | −0.08/−0.07 |
| Anionic | 0.3% TCS | 2.5% potassium oleate (KO) | 0.26/0.52 | −0.23/−0.23 |
| | 0% TCS | 2.5% potassium oleate (KO) | −0.15/−0.10 | −0.30/0.026 |
| Anionic | 0.3% TCS | 2.0% potassium laurate (KL) | 3.08/3.61 | 0.10/−0.27 |
| Anionic | 0.3% TCS | 3.0% potassium laurate (KL) | 1.06/1.86 | 0.82/3.02 |
| | 0% TCS | 3.0% potassium laurate (KL) | 0.18/0.21 | 1.74/>4.40 |
| | | Series IV--EO-Containing Surfactants | | |
| Anionic/ Nonionic | 0.3% TCS | 1.25% sodium lauryl ether sulfate, 1-mole EO (SLES-1) | >4.39/>4.39 | 0.41/0.46 |
| Anionic/ Nonionic | 0.3% TCS | 1% sodium lauryl ether sulfate, 2-mole EO (SLES-2) | >4.24/>4.25 | 0/0.12 |
| Anionic/ Nonionic | 0.3% TCS | 2.0% sodium myreth-4 carboxylate (NaNDX23-4) | −0.49/−0.49 | −0.19/−0.19 |
| Nonionic | 0.3% TCS | 4% octoxynol-9 (TX100) | 0.16/0.15 | 0.43/0.46 |
| | | Series V--Miscellaneous Surfactants | | |
| Cationic | 0.3% TCS | 1.5% lauramine oxide (LAO) | >4.25/>4.25 | >4.63/>4.63 |
| | 0% TCS | 1.5% lauramine oxide (LAO) | 3.55/3.86 | 4.18/4.73 |
| Anionic | 0.3% TCS | 1.25% sodium lauroyl sarcosinate (SLSarc) | 4.04/>4.34 | −0.05/0.04 |
| Anionic | 0.3% TCS | 1.5% disodium lauryl sulfosuccinate (DSLrylScct) | 2.95/4.06 | 0.02/0.16 |
| Nonionic/ Anionic | 0.3% TCS | 1.25% disodium laureth sulfosuccinate (DSLScct) | 1.76/2.68 | 0.36/0.38 |
| Anionic | 0.3% TCS | 1% sodium lauryl sulfoacetate (SLSA) | 3.19/3.83 | −0.09/−0.03 |
| Anionic | 0.3% TCS | 2.0% methyl ester sulfonate (MES) | >4.64/>4.64 | 0.11/0.22 |
| Anionic | 0.3% TCS | 1.25% alpha-olefin sulfonate (AOS) | 1.34/— | 0.28/0.33 |
| Anionic | 0.3% TCS | 3% C10 (linear) sodium diphenyl oxide disulfonate (L10-45) | 2.77/4.04 | 0.18/0.23 |
| Amphoteric | 0.3% TCS | 1.25% sodium cocoamphoacetate (SCA) | −0.15/−0.20 | −0.17/−0.15 |
| Amphoteric | 0.3% TCS | 1.75% cocamidoproyl betaine (CAPP) | −0.09/−0.03 | 0.21/0.61 |
| Nonionic | 0.3% TCS | 2.5% alkyl polyglucose (APG) | −0.10/−0.17 | 0.01/−0.02 |

EXAMPLE 6

This example illustrates the effect of % saturation of TCS in surfactant compositions (i.e., compositions free of a hydric solvent and hydrotrope). The data summarized in the following table illustrate the effect of % saturation of TCS on the efficacy of TCS in TCS/surfactant/water compositions. Two sections of the table (i.e., TCS/ALS compositions vs. E. coli and TCS/SOS compositions vs. S. aureus) show a substantial decrease in antibacterial activity with decreasing % saturation. Also, 100% saturated samples (0.15%TCS/0.67%ALS) and (0.15%TCS/4.0%SOS) have an antibacterial activity approaching that of 100% saturated samples containing 0.3% TCS. In these two examples, the effects are seen clearly for organisms wherein the surfactant does not show a strong placebo kill effect.

Effect of % TCS Saturation on Antibacterial Efficacy

| TCS %/ % Sat'n | Surfactant | Log Reduction | | |
|---|---|---|---|---|
| | | S. aureus (30s/1 min) | E. coli (30s/1 min) | K. pneum. (30s/1 min) |
| 0.30/100 | 1.35% ALS | >3.97/>3.97 | 1.39/3.95 | |
| 0.27/90 | 1.35% ALS | >3.97/>3.97 | 0.61/2.89 | |
| 0.21/70 | 1.35% ALS | >3.97/>3.97 | 0.37/1.54 | |
| 0.15/50 | 1.35% ALS | >3.97/>3.97 | 0.09/1.17 | |
| 0.15/100 | 0.67% ALS | >3.97/>3.97 | 1.10/3.63 | |
| 0/0 | 1.35% ALS | >3.97/>3.97 | −0.07/−0.02 | |
| 0.30/100 | 1.60% SLS | >3.94/>3.94 | 4.36/4.36 | |
| 0.27/90 | 1.60% SLS | >3.94/>3.94 | 4.36/>4.46 | |
| 0.21/70 | 1.60% SLS | >3.94/>3.94 | 4.04/>4.46 | |
| 0.15/50 | 1.60% SLS | >3.94/>3.94 | 4.13/>4.46 | |
| 0.15/100 | 0.80% SLS | >3.94/>3.94 | 3.17/>4.46 | |
| 0/0 | 1.60% SLS | >3.94/>3.94 | 1.51/2.96 | |
| 0.30/100 | 5.75% SOS | 3.39/3.04 | | >4.44/3.98 |
| 0.27/90 | 5.75% SOS | 2.59/3.04 | | >4.44/>4.44 |
| 0.21/70 | 5.75% SOS | 1.59/1.82 | | >4.44/>4.44 |
| 0.15/50 | 5.75% SOS | 0.96/1.43 | | >4.44/>4.44 |
| 0.15/100 | 4.00% SOS | 2.90/3.20 | | >4.44/>4.44 |
| 0/0 | 5.75% SOS | 0.23/0.30 | | >4.44/>4.44 |

EXAMPLE 7

This example illustrates a composition of the present invention that can be used as a hand cleanser. This example further illustrates an embodiment of the invention wherein the antibacterial agent is present in combination with a surfactant, hydric solvent, and hydrotrope. Composition A-5 contains, by weight, 0.3% triclosan, 0.5% ammonium lauryl sulfate, 20% propylene glycol, and 10% sodium xylene sulfonate, with the balance water. Composition A-6, by weight, contains 0.1% triclosan, 0.125% ammonium xylene sulfonate, 20% propylene glycol, and 10% sodium xylene sulfonate the balance being water. Compositions A-5 and A-6 were 100% saturated with triclosan. Composition A-7 was a "placebo" containing, by weight, 0.5% ammonium lauryl sulfate, 20% propylene glycol, 10% sodium xylene sulfate, and the balance being water.

| Product | Triclosan % | % Saturation | Log Reduction at 30 seconds (time kill) | | | |
|---|---|---|---|---|---|---|
| | | | S. aureus | E. coli | K. pneum. | S. chol. |
| A-5 | 0.3 | 100 | >3.84 | >4.41 | 3.56 | 3.26 |
| A-6 | 0.1 | 100 | >3.84 | >4.41 | 3.82 | 3.95 |
| A-7 | 0.0 | 0 | 3.22 | 3.36 | 0.74 | 1.77 |

This example illustrates two important features of the present invention. First, the absolute amount of triclosan, or other antibacterial agent, is less important than the percent saturation of antibacterial agent in the composition. For example, composition A-6 (containing 0.10% triclosan) was at least as effective as composition A-5 (containing 0.3% triclosan). The important feature is that both compositions were 100% saturated with triclosan. Second, Example 5 also clearly showed that the active antibacterial agent is responsible for the excellent broad spectrum antibacterial activity. Compositions A-S and A-6 of the invention clearly outperformed the "placebo" composition A-7, which did not contain an active antibacterial agent.

EXAMPLE 8

This example demonstrates that a hydric solvent and hydrotrope can impart activity to an otherwise inactive surfactant and antibacterial agent composition. In the following table, all percentages are by weight, and the balance of all compositions is water. Composition B contains 1.35% ammonium lauryl sulfate (ALS) and 0.3% triclosan (TCS). Composition C contains 1.35% ALS and 0.0% TCS. Composition D contains 0.25% ALS, 14.4% DPG, 10.0% SXS, and 0.3% TCS, and Composition E contains 0.25% ALS, 14.4% DPG, 10.0% SXS with 0.0% TCS. Compound F contains 2.5% alkyl polyglucoside (APG™) with 0.3% TCS. Compound G contains 0.3% APG, 14.4% dipropylene glycol (DPG), 10% sodium xylene sulfonate (SXS), and 0.3% TCS. Compound H contains 0.3% APG with 14.4% DPG, 10% SXS, and 0.0% TCS. Composition I contains 1.25% sodium cocoamphoacetate (SCA) and 0.3% TCS. Composition J contains 0.25% SCA, 14.4% DPG, 10.0% SXS, and 0.3% TCS. Composition K contains 0.25% SCA, 14.4% DPG, 10.0% SXS, and 0.0% TCS. Composition L contains 1.75% cocamidopropyl betaine (CAPB) and 0.3% TCS. Composition M contains 0.25% CAPB, 14.49% DPG, 10% SXS, and 0.3% TCS. Composition N contains 0.25% CAPB, 14.4% DPG, 10% SXS, and 0.0% TCS. Composition 0 contains 4% octoxynol-9 (TRITON X-100™, TX100). Composition P contains 0.75% TX100, 14.4% DPG, 10.0% SXS, and 0.3% TCS. Composition Q contains 1.25% sodium lauryl ether sulfate (1 EO, SLES-1) and 0.3% TCS. Composition R contains 0.25% SLES-1, 14.4% DPG, 10.0% SXS, and 0.3% TCS.

| Composition | Triclosan % | Other Ingredients | % Saturation | Log Reduction (Time Kill) S. aureus (30s/60s) | Log Reduction (Time Kill) E. coli (30s/60s) |
|---|---|---|---|---|---|
| B | 0.3 | 1.35%ALS | ~100 | >3.97/>3.97 | 1.39/3.95 |
| C | 0.0 | 1.35%ALS | 0 | >3.97/>3.97 | −0.07/−0.02 |
| D | 0.3 | 0.25%ALS, 14.4%DPG, 10.0%SXS | ~100 | >3.80/>3.80 | >4.38/>4.38 |
| E | 0.0 | 0.25%ALS, 14.4%DPS, 10.0%SXS | ~100 | 1.31/1.54 | >2.49/>4.18 |
| F | 0.3 | 2.5%APG | ~100 | 1.19/1.21 | >4.69/>4.69 |
| G | 0.3 | 0.3%APG, 14.4%DPG, 10.0%SXS | ~100 | >4.69/>4.69 | 4.50/4.58 |
| H | 0.0 | 0.3%APG, 14.4%DPG, 10.0%SXS | 0 | 1.19/1.21 | >4.69/>4.69 |
| I | 0.3 | 1.25%SCA | ~100 | −0.15/−0.20 | −0.17/−0.15 |
| J | 0.3 | 0.25%SCA, 14.4%DPG, 10.0%SXS | ~100 | >4.39/>4.39 | >4.73/>4.73 |
| K | 0.0 | 0.25%SCA, 14.4%DPG, 10.0%SXS | 0 | 0.86/0.88 | 2.90/4.05 |
| L | 0.3 | 1.75%CAPB | ~100 | −0.09/−0.03 | 0.21/0.61 |
| M | 0.3 | 0.25%CAPB, 14.4%DPG, 10.0%SXS | ~100 | >4.39/>4.39 | >4.73/>4.73 |
| N | 0.0 | 0.25%CAPB, 14.4%DPG, 10.0%SXS | 0 | 0.76/0.85 | 3.26/4.69 |
| O | 0.3 | 4%TX100 | ~100 | 0.16/0.15 | 0.43/0.46 |
| P | 0.3 | 0.75%TX100, 14.4%DPG, 10.0%SXS | ~100 | 0.53/0.58 | 3.59/>4.73 |
| Q | 0.3 | 1.25%SLES-1 | ~100 | >4.39/>4.39 | 0.41/0.46 |
| R | 0.3 | 0.25%SLES-1, 14.4%DPG, 10.0%SXS | ~100 | >4.34/>4.84 | >4.47/>4.47 |

The results of the time kill tests summarized in the above table very surprisingly show that the use of a hydric solvent and hydrotrope can impart a high antibacterial activity to surfactant/TCS combinations which alone exhibit only low to moderate efficacy (i.e., compare efficacy of composition F vs. G; I vs. J; L vs. M; and Q vs. R). The hydric solvent and hydrotrope also can render active compositions more active in shorter contact times (i.e., compare composition B vs. D). Especially surprising is the observation that a hydric solvent and hydrotrope can impart antibacterial efficacy against *E. coli* even in a composition containing a nonionic surfactant, i.e., octoxynol-9 (compare compositions O vs. P). This result is unexpected because polyethoxylated surfactants are known to inactivate phenolic antibacterial agents.

EXAMPLE 9

This example demonstrates the importance of % saturation in compositions containing a hydric solvent and hydrotrope. As observed in surfactant/TCS compositions, the relative % saturation of the antibacterial agent in the continuous aqueous phase of the composition also greatly influences the antibacterial activity of compositions containing a hydric solvent and hydrotrope. As the results summarized below illustrate, this influence on antibacterial activity is especially apparent with respect to the Gram negative bacterium, *K. pneum*.

| Composition | Triclosan % | Other Ingredients | % Saturation |
|---|---|---|---|
| S | 0.3 | 0.25%ALS, 14.4%DPG, 10.0%SXS | ~100 |
| T | 0.3 | 0.50%ALS, 14.4%DPG, 10.0%SXS | <S |
| U | 0.3 | 1.00%ALS, 14.4%DPG, 10.0%SXS | <S, T |
| V | 0.0 | 1.00%ALS, 14.4%DPG, 10.0%SXS | 0 |
| W | 0.3 | 1.20%ALS, 2.5%DPG, 10.0%SXS | ~100 |
| X | 0.3 | 2.5%ALS, 2.5%DPG, 10.0%SXS | <W |
| Y | 0.3 | 5.0%ALS, 2.5%DPG, 10.0%SXS | <W, X |
| Z | 0.0 | 5.0%ALS, 2.5%DPG, 10.0%SXS | 0 |

| Composition | Log Reduction (time kill) S. aureus (30s/60s) | Log Reduction (time kill) E. coli (30s/60s) | Log Reduction (time kill) K. pneum. (30s/60s) | Log Reduction (time kill) S. chol. (30s/60s) |
|---|---|---|---|---|
| S | >3.62/>3.62 | >4.59/>4.59 | 2.64/>3.84 | >3.85/>3.85 |
| T | >3.62/>3.62 | >4.59/>4.59 | 2.43/3.69 | >3.85/>3.85 |
| U | 1.67/2.31 | >4.59/>4.59 | 0.89/1.93 | 3.50/>3.85 |
| V | 1.10/1.29 | 3.42/4.59 | 0.28/0.67 | 2.17/>3.85 |
| W | — | — | — | 4.19/4.39 |
| X | — | — | — | 2.83/3.99 |
| Y | — | — | — | 2.39/3.22 |
| Z | — | — | — | 1.80/2.52 |

From the above data, it is clear that an increase in antibacterial efficacy, as measured by a time kill test, is associated with an increasing % saturation of the antibacterial agent in the aqueous phase of a given composition. This example further shows that compositions containing an antibacterial agent, surfactant, hydric solvent, and hydrotrope are effective when a high % saturation of active antibacterial agent is maintained.

EXAMPLE 10

This example, in conjunction with Example 9, illustrates the effect of % saturation of TCS in compositions containing a hydric solvent, hydrotrope, and surfactant. As previously observed with simple surfactant/TCS compositions, the relative % saturation of the antibacterial agent in the composition also influences the antibacterial activity of a composition containing a hydric solvent and/or a hydrotrope. From the data summarized in the table of Example 9 and the following table, it is clear that a substantial gain in antibacterial efficacy (as measured by a time kill test) is associated with an increasing % saturation of the antibacterial agent in a given type of composition. The tables demonstrate this effect from two different perspectives. The table in Example 9 shows the effect of changing the concentration of surfactant while maintaining the amount of other composition components constant. The following table shows the effect of varying the concentration of TCS while the concentration of all other components is kept constant. In the table of Example 9, the information relating to % saturation is relative because % saturation is difficult to directly calculate. Even using this qualitative data, the effect of % saturation of TCS is clear from both tables for all organisms tested.

perfume (PF) and/or a preservative (DMDM) to the composition has only a modest effect, if any, on the antibacterial efficacy of the compositions.

Activity Dependence on % Saturation of TCS in Hydric Solvent/Hydrotrope/Surfactant Compositions

| | | | Log Reduction (Time Kill) | |
|---|---|---|---|---|
| Triclosan % | Other Ingredients | % Saturation | S. aureus (30s/60s) | K. pneum. (30s/60s) |
| 0.413 | 5%DPG, 15%SXS, 0.75%ALS | 100 | >4.55/>4.55 | >3.81/>3.81 |
| 0.372 | 5%DPG, 15%SXS, 0.75%ALS | 90 | >4.55/>4.55 | 3.81/>3.81 |
| 0.330 | 5%DPG, 15%SXS, 0.75%ALS | 80 | >4.55/>4.55 | 3.46/>3.81 |
| 0.300 | 5%DPG, 15%SXS, 0.75%ALS | 73 | >4.55/>4.55 | 3.40/>3.81 |
| 0.248 | 5%DPG, 15%SXS, 0.75%ALS | 60 | 3.02/4.05 | 2.73/>3.81 |
| 0.207 | 5%DPG, 15%SXS, 0.75%ALS | 50 | 1.96/3.05 | 2.45/>3.81 |
| 0.166 | 5%DPG, 15%SXS, 0.75%ALS | 40 | 1.94/2.15 | 2.30/>3.81 |
| 0.103 | 5%DPG, 15%SXS, 0.75%ALS | 25 | 1.72/1.93 | 1.34/2.78 |

EXAMPLE 11

This example illustrates the effect of different levels of hydric solvent and hydrotrope on antibacterial efficacy. In particular, the data summarized below demonstrates the effect of varying the relative amounts of hydric solvent and hydrotrope. It should further be noted that the addition of a

| | | | Log Reduction (Time Kill) | | | |
|---|---|---|---|---|---|---|
| Composition | Triclosan % | Other Ingredients | S. aureus (30s/60s) | E. coli (30s/60s) | K. pneum. (30s/60s) | S. choler. (30s/60s) |
| CCC | Calc 0.0502 | 14.5%DPG, 10.0%SXS | >3.63/>3.63 | >4.44/>4.44 | >4.14/>4.14 | >4.14/>4.14 |
| DDD | 0.0 | 14.5%DPG, 10.0%SXS | 0.03/0.04 | 0.26/0.17 | 0.34/0.39 | 0.36/0.47 |
| E | 0.0 | 0.25%ALS, 14.4%DPG, 10.0%SXS | 1.31/1.54 | 2.49/4.18 | 0.41/0.78 | 2.62/>4.04 |
| S | 0.3 | 0.25%ALS, 14.4%DPG, 10.0%SXS | >3.62/>3.62 | >4.59/>4.59 | 2.64/>3.84 | >3.85/>3.85 |
| T | 0.3 | 0.50%ALS, 14.4%DPG, 10.0%SXS | >3.62/>3.62 | >4.59/>4.59 | 2.43/3.69 | >3.85/>3.85 |
| U | 0.3 | 1.00%ALS, 14.4%DPG, 10.0%SXS | 1.67/2.31 | >4.59/>4.59 | 0.89/1.93 | 3.50/>3.85 |
| V | 0.0 | 1.00%ALS, 14.4%DPG, 10.0%SXS | 1.10/1.29 | 3.42/4.59 | 0.28/0.67 | 2.17/>3.85 |
| AA | 0.3 | 0.75%ALS, 5.0%DPG, 10.0%SXS | | | 0.95/2.00 | |
| BB | 0.3 | 0.75%ALS, 5.0%DPG, 12.5%SXS | | | 1.77/3.36 | |
| CC | 0.3 | 0.75%ALS, 5.0%DPG, 15.0%SXS | | | 3.49/>3.69 | |
| DD | 0.3 | 0.75%ALS, 5.0%DPG, 17.5%SXS | | | >3.69/>3.69 | |
| EE | 0.3 | 0.75%ALS; 5.0%DPG, 20.0%SXS | | | >3.69/>3.69 | |
| FF | 0.3 | 0.75%ALS, 7.5%DPG, 10.0%SXS | | | 0.81/2.87 | |
| GG | 0.3 | 0.75%ALS, 7.5%DPG, 12.5%SXS | | | 1.72/4.21 | |
| HH | 0.3 | 0.75%ALS, 7.5%DPG, 15.0%SXS | | | 3.04/4.31 | |
| II | 0.3 | 0.75T%ALS, 7.5%DPG, 17.5%SXS | | | >4.41/>4.41 | |
| JJ | 0.3 | 0.75%ALS, 7.5%DPG, 20.0%SXS | | | >4.41/>4.41 | |
| KK | 0.3 | 1.0%ALS, 5.0%DPG, 10.0%SXS | | | 0.08/1.49 | |
| LL | 0.3 | 1.0%ALS, 5.0%DPG, 12.5%SXS | | | 0.97/3.32 | |
| MM | 0.3 | 1.0%ALS, 5.0%DPG, 15.0%SXS | | | 2.57/>4.41 | |
| NN | 0.3 | 1.0%ALS, 5.0%DPG, 17.5%SXS | | | >4.41/>4.41 | |
| OO | 0.3 | 1.0%ALS, 5.0%DPG, 20.0%SXS | | | >4.41/>4.41 | |
| PP | 0.3 | 1.0%ALS, 7.5%DPG, 10.0%SXS | | | 0.17/0.92 | |
| QQ | 0.3 | 1.0%ALS, 7.5%DPG, 12.5%SXS | | | 0.92/2.94 | |
| RR | 0.3 | 1.0%ALS, 7.5%DPG, 15.0%SXS | | | 2.92/>3.69 | |
| SS | 0.3 | 1.0%ALS, 7.5%DPG, 17.5%SXS | | | >3.69/>3.69 | |
| TT | 0.3 | 1.0%ALS, 7.5%DPG, 20.0%SXS | | | >3.69/>3.69 | |
| UU | 0.3 | 0.75%ALS, 5.0%DPG, 15.0%SXS | 3.79/>4.64 | >4.57/>4.57 | 4.07/>4.69 | >3.97/>3.97 |
| VV | 0.3 | 0.75%ALS, 5.0%DPG, 15.0%SXS | 3.07/3.76 | 4.01/>4.34 | 3.40/>4.46 | >4.04/>4.04 |
| WW | 0.0 | 0.75%ALS, 5.0%DPG, 15.0%SXS | 0.79/0.90 | >4.34/>4.34 | 0.41/1.53 | >4.04/>4.04 |
| XX | 0.3 | 0.75%ALS, 10.0%DPG, 10.0%SXS | | >4.78/>4.78 | 0.67/1.46 | |
| YY | 0.3 | 0.75%ALS, 10.0%DPG, 20.0%SXS | | >4.78/>4.78 | >4.17/>4.17 | |
| ZZ | 0.0 | 0.75%ALS, 10.0%DPG, 20.0%SXS | | >4.78/>4.78 | >4.17/>4.17 | |
| AAA | 0.3 | 0.75%ALS, 14.4%DPG, 10%SXS | | >4.95/>4.95 | | |
| BBB | 0.0 | 0.75%ALS, 14.4%DPG | | 0.28/0.28 | | |

It was observed that for compositions S, T, and U, the antibacterial activity against S. aureus and K. pneum. increases, especially, with a decreasing wt % of ALS surfactant (i.e., an increase in % saturation of TCS). Compositions CC, HH, MM, and RR demonstrate that about 15% SXS, or more, is preferred to exhibit high activity against *K. pneum.* in compositions containing a hydric solvent and a hydrotrope. This observation suggests that the hydrotrope may be acting as an adjuvant for the TCS because the time required for a substantial antibacterial kill, i.e., log reduction of at least 2, is reduced.

EXAMPLE 12

The data summarized in the following table support a theory that the two primary factors for improved antibacterial efficacy are the relative amounts of surfactant and hydrotrope to the amount of antibacterial agent in compositions containing a surfactant, hydric solvent, and antibacterial agent. A higher percentage of surfactant can reduce the % saturation, and thereby decrease the antimicrobial activity of the composition. On the other hand, a higher percentage of hydrotrope appears to provide a higher activity against certain organisms, like *K. pneum.* and *S. choler.* It is theorized that the higher percentage of hydrotrope in the composition provides a greater amount of active antibacterial compound in the aqueous (i.e., nonmicellar) phase of the composition, thereby providing a higher time kill activity. The solvent, therefore, may be acting as both an additive to enhance antimicrobial activity and to provide better physical stability in these compositions.

| | | | Log Reduction (Time Kill) | | | |
|---|---|---|---|---|---|---|
| Composition | Triclosan % | Other Ingredients | S. aureus (30s/60s) | E. coli (30s/60s) | K. pneum. (30s/60s) | S. choler. (30s/60s) |
| CCC | Calc. 0.0502 | 14.5%DPG, 10.0%SXS | >3.63/>3.63 | >4.44/>4.44 | >4.14/>4.14 | >4.14/>4.14 |
| DDD | 0.0 | 14.5%DPG, 10.0%SXS | 0.03/0.04 | 0.26/0.17 | 0.34/0.39 | 0.36/0.47 |
| EEE | 0.3%TCS | 0.25%ALS, 14.4%DPG, 10.0%SXS | >3.80/>3.80 | >4.38/>4.38 | 3.54/>4.07 | >4.04/>4.04 |
| FFF | 0%TCS | 0.25%ALS, 14.4%DPG, 10.0%SXS | 1.31/1.54 | 2.49/4.18 | 0.41/0.78 | 2.62/>4.04 |
| GGG | 0.3%TCS | 0.25%ALS, 14.4%DPG, 10.0%SXS | >3.62/>3.62 | >4.59/>4.59 | 2.64/>3.84 | >3.85/>3.85 |
| HHH | 0.3%TCS | 0.5%ALS, 14.4%DPG, 10.0%SXS | >3.62/>3.62 | >4.59/>4.59 | 2.43/3.69 | >3.85/>3.85 |
| III | 0.3%TCS | 1%ALS, 14.4%DPG, 10.0%SXS | 1.67/2.31 | >4.59/>4.59 | 0.89/1.93 | 3.50/>3.85 |
| JJJ | 0%TCS | 1%ALS, 14.4%DPG, 10.0%SXS | 1.10/1.29 | 3.42/4.59 | 0.28/0.67 | 2.17/>3.85 |
| KKK | 0.4%TCS | 0.25%ALS, 14.4%DPG, 10.0%SXS, 0.05%PF | >4.59/>4.59 | >4.70/>4.70 | 4.11/>4.41 | >4.04/>4.04 |
| LLL | 0.3%TCS | 0.25%ALS, 14.4%DPG, 10.0%SXS, 0.05%PF | >4.59/>4.59 | >4.70/>4.70 | 4.06/>4.41 | >4.04/>4.04 |
| MMM | 0%TCS | 0.25%ALS, 14.4%DPG, 10.0%SXS, 0.05%PF | 1.70/2.19 | 3.97/>4.70 | 0.50/1.43 | 3.04/>4.04 |
| NNN | 0.3%TCS | 0.25%ALS, 14.4%DPG, 10.0%SXS, 0.05%PF | >4.77/4.57 | >4.71/>4.71 | 3.90/>4.55 | >4.20/>4.20 |
| OOO | 0.3%TCS | 1%ALS, 14.4%DPG, 10.0%SXS, 0.5%PF | 3.18/4.09 | >4.71/>4.71 | 1.11/3.62 | 3.90/>4.20 |
| PPP | 0.3%TCS | 0.5%ALS, 14.4%DPG, 10.0%SXS, 0.05%PF | 4.39/>4.77 | >4.71/>4.71 | 3.00/>4.55 | >4.20/>4.20 |
| QQQ | 0%TCS | 1%ALS, 14.4%DPG, 10.0%SXS, 0.05%PF | 2.42/3.07 | 3.03/>4.71 | 0.65/0.98 | 2.29/4.10 |
| RRR | 0.3%TCS | 0.5%ALS, 14.4%DPG, 10.0%SXS, 0.05%PF | >4.71/>4.71 | >4.61/>4.61 | 2.10/3.97 | >3.87/>3.87 |
| SSS | 0.3%TCS | 0.6%ALS, 14.4%DPG, 10.0%SXS, 0.05%PF | >4.71/>4.71 | 4.61/>4.61 | 1.46/3.62 | >3.87/>3.87 |
| TTT | 0.3%TCS | 0.75%ALS, 14.4%DPG, 10.0%SXS, 0.05%PF | 4.28/>4.71 | >4.61/>4.61 | 1.42/3.34 | >3.87/>3.87 |
| UUU | 0.3%TCS | 0.35%ALS, 10.0%DPG, 10.0%SXS, 0.05%PF | >4.23/>4.23 | >4.62/>4.62 | 3.30/4.63 | >3.87/>3.87 |
| VVV | 0.3%TCS | 0.5%ALS, 10.0%DPG, 10.0%SXS, 0.05%PF | >4.23/>4.23 | >4.62/>4.62 | 2.86/4.18 | >3.87/>3.87 |
| WWW | 0.3%TCS | 0.5%ALS, 7.5%DPG, 10.0%SXS, 0.05%PF | >4.23/>4.23 | >4.62/>4.62 | 2.63/3.77 | >3.87/>3.87 |
| XXX | 0.3%TCS | 0.6%ALS, 7.5%DPG, 10.0%SXS, 0.05%PF | >4.23/>4.23 | >4.62/>4.62 | 2.45/3.15 | >3.87/>3.87 |
| YYY | 0.3%TCS | 0.5%ALS, 14.4%DPG, 10.0%SXS, 0.05%PF, 0.25%DMDM | >3.83/>3.83 | >4.41/>4.41 | 2.89/>3.76 | >3.59/>3.59 |
| ZZZ | 0%TCS | 0.5%ALS, 14.4%DPG, 10.0%SXS, 0.05%PF, 0.25%DMDM | 1.48/2.10 | 3.84/>4.41 | 0.38/1.12 | 2.09/3.45 |
| AAAA | 0.3%TCS | 0.75%ALS, 5.0%DPG, 10.0%SXS, 0.05%PF | >4.07/>4.07 | 3.90/4.03 | 1.97/3.66 | 3.24/3.24 |
| BBBB | 0.3%TCS | 0.75%ALS, 5.0%DPG, 7.5%SXS, 0.05%PF | >4.07/>4.07 | 3.10/4.28 | 0.25/2.23 | 0.91/2.80 |
| CCCC | 0.3%TCS | 0.75%ALS, 7.5%DPG, 10.0%SXS, 0.05%PF | >4.07/>4.07 | 3.82/4.53 | 1.49/3.56 | 2.93/>3.34 |

-continued

| Composition | Triclosan % | Other Ingredients | Log Reduction (Time Kill) | | | |
|---|---|---|---|---|---|---|
| | | | S. aureus (30s/60s) | E. coli (30s/60s) | K. pneum. (30s/60s) | S. choler. (30s/60s) |
| DDDD | 0.3%TCS | 0.75%ALS, 7.5%DPG, 7.5%SXS, 0.05%PF | >4.07/>4.07 | 3.47/4.18 | 0.19/2.00 | 0.99/2.76 |

EXAMPLE 13

This example shows that other hydric solvents can be used in a composition of the present invention.

minimum level of hydrotrope may be needed for a high antibacterial efficacy against at least some Gram negative bacteria.

| Composition | Triclosan % | Other Ingredients | Log Reduction (Time Kill) | | | |
|---|---|---|---|---|---|---|
| | | | S. aureus (30s/60s) | E. coli (30s/60s) | K. pneum. (30s/60s) | S. choler. (30s/60s) |
| EEEE | 0.3 | 0.75%ALS, 5.0% tripropylene glycol (TPG), 10.0%SXS | 4.24.3.91 | >4.73/>4.73 | — | — |
| FFFF | 0.3 | 0.75%ALS, 10.0%TPG, 10.0%SXS | 2.59/3.65 | >4.73/>4.73 | — | — |
| GGGG | 0.0 | 0.75%ALS, 10.0%TPG, 10.0%SXS | 0.77/1.11 | 3.60/4.40 | — | — |
| HHHH | 0.3 | 0.75%ALS, 14.4% propylene glycol (PG), 10.0%SXS | >4.44/>4.44 | 4.58/>4.78 | — | — |
| IIII | 0.3 | 1.0%ALS, 10.0%PG, 10.0%SXS | >4.44/>4.44 | 4.48/>4.78 | — | — |
| JJJJ | 0.3 | 0.5%ALS, 20.0%PG, 10.0%SXS | >3.99/>3.99 | >4.45/>4.55 | 3.66/>4.04 | 3.23/>3.68 |
| KKKK | 0.1 | 0.5%ALS, 20.0%PG, 10.0%SXS | >3.99/>3.99 | 3.75/>4.55 | 1.08/3.13 | 1.51/2.84 |
| LLLL | 0.0 | 0.5%ALS, 20.0%PG, 10.0%SXS | >3.99/>3.99 | 2.58/4.14 | 0.25/.072 | 1.28/2.36 |
| MMMM | 0.1 | 0.12%ALS, 20.0%PG, 10.0%SXS | >3.84/>3.84 | >4.41/>4.41 | 3.82/>3.92 | 3.95/>3.95 |
| NNNN | 0.3 | 0.5%ALS, 20.0%PG, 10.0%SXS | >3.84/>3.84 | >4.41/>4.41 | 3.56/>3.92 | 3.26/>3.95 |
| OOOO | 0.0 | 0.5%ALS, 20.0%PG, 10.0%SXS | 3.22/3.84 | 3.36/>4.41 | 0.74/1.49 | 1.77/2.93 |
| PPPP | 0.3 | 0.8%SLS, 10.0%PG, 5.0%SXS | >4.11/>4.11 | 2.50/>3.61 | — | — |
| QQQQ | 0.0 | 0.8%SLS, 10.0%PG, 5.0%SXS | 2.67/3.91 | 1.19/2.40 | — | — |
| RRRR | 0.3 | 0.8%ALS, 10.0%PG, 5.0%SXS | >4.11/>4.11 | 1.66/3.25 | — | — |
| SSSS | 0.0 | 0.8%ALS, 10.0%PG, 5.0%SXS | 2.28/3.03 | 0.79/1.63 | — | — |
| TTTT | 0.26 | 0.9%ALS, 10.0%PG, 5.0%SXS | >4.24/>4.25 | 0.16/0.93 | −0.02/0.07 | 0.53/0.33 |
| UUUU | 0.0 | 0.9%ALS, 10.0%PG, 5.0%SXS | 2.53/>4.25 | 0.06/0.21 | 0.10/0.00 | 0.17/0.13 |

In addition to the observation that other solvents (e.g., PG and TPG) can be used in compositions of the present invention, products JJJJ through OOOO illustrate another effect of relative saturation of antibacterial agent in the system. The relative % saturation (highest to lowest) of the first three compositions is JJJJ>KKKK>LLLL. Composition KKKK has one-third the amount of TCS as composition JJJJ solubilized in the same level of ALS (0.5%), and compositions LLLL contains 0% TCS. Significant reductions in activity were observed with respect to K. pneum. and S. choler. when the relative % saturation of TCS in the composition decreases. It also was observed that when the relative % saturation is essentially equal (i.e., about 100%), the activity remains essentially constant even though the absolute amount of TCS in the composition is decreased (i.e., compare Compositions MMMM to NNNN). These data further support the observations with respect to the importance of % saturation set forth in Example 6.

In addition, a comparison of composition IIII to composition TTTT shows that composition TTTT contains slightly less ALS (0.9% vs. 1.0% for IIII), the same amount of PG (10.0%), and one-half the amount of SXS (5.0% vs. 10.0% for IIII). Experimental observations indicated that compositions IIII and TTTT were at or near 100% saturation. However, the log reductions of E. coli were considerably lower (about 4 log) for Composition TTTT. This observation further supports the data set forth in Example 7 wherein The data presented in all the above tables show that % saturation of antibacterial agent in the aqueous phase of the composition can be directly correlated to a log reduction of bacteria. For example, as shown in the prior tables, a composition having 50% saturation of TCS in the aqueous phase demonstrates a log reduction versus S. aureus of 1.96 (30 seconds) and 3.05 (60 seconds) and a log reduction versus E. coli of 2.45 (30 seconds) and greater than 3.81 (60 seconds). A 75% saturated and a 100% saturated composition exhibited a log reduction of greater than 4.55 (30 and 60 seconds) vs. S. aureus (i.e., a log reduction in excess of the detection limit of the assay). The 75% and 100% saturated compositions exhibited a log reduction of 3.40 (30 seconds) and greater than 3.81 (60 seconds) and greater than 3.81 (30 and 60 seconds) vs. E. coli, respectively. Accordingly, the present antibacterial compositions can be characterized as exhibiting a log reduction of at least about 2 (after 30 seconds) or at least about 3 (after 60 seconds) vs. S. aureus, or of at least about 2.5 (after 30 seconds) or at least about 3.5 (after 60 seconds) vs. E. coli.

The antibacterial compositions of the present invention have several practical end uses, including hand cleansers, mouthwashes, surgical scrubs, body splashes, hand sanitizer gels, and similar personal care products. Additional types of compositions include foamed compositions, such as creams, mousses, and the like, and compositions containing organic and inorganic filler materials, such as emulsions, lotions, creams, pastes, and the like. The compositions further can be used as an antibacterial cleanser for hard surfaces, for example, sinks and countertops in hospitals, food service areas, and meat processing plants. The present antibacterial compositions can be manufactured as dilute ready-to-use compositions, or as concentrates that are diluted prior to use.

The compositions also can be incorporated into a web material to provide an antibacterial wiping article. The wiping article can be used to clean and sanitize skin or inanimate surfaces.

The present antimicrobial compositions provide the advantages of a broad spectrum kill of Gram positive and Gram negative bacteria in short contact times. The short contact time for a substantial log reduction of bacteria is important in view of the typical 15 to 60 second time frame used to cleanse and sanitize the skin and inanimate surfaces.

The present compositions are effective in short contact time because the antibacterial agent is present in the aqueous continuous phase of the composition, as opposed to surfactant micelles. The antibacterial agent, therefore, is available to immediately begin reducing bacterial populations, and further is available to deposit on the skin to provide residual antibacterial efficacy. In addition, because the antibacterial agent is in solution as opposed to surfactant micelles, the absolute amount of antimicrobial agent in the composition can be reduced without adversely affecting efficacy, and the antibacterial agent is not rinsed from the skin with the surfactant prior to performing its antibacterial function. In addition, the amount of surfactant in the present antibacterial compositions typically is low, thereby providing additional environmental benefits.

The following examples illustrate various compositions of the present invention.

EXAMPLE 14

Hand Wash Composition

A composition in accordance with the instant invention, suitable for use as a hand wash, was prepared. The composition contained the following components in the indicated weight percentages:

| Ingredient | Weight Percent |
| --- | --- |
| Triclosan | 0.3 |
| Ammonium Lauryl Sulfate | 0.75 |
| Dipropylene Glycol | 5.0 |
| Sodium Xylene Sulfonate | 10.0 |
| Fragrance | 0.05 |
| Water | q.s. |

The composition was prepared by admixing the dipropylene glycol, TCS, and fragrance until homogeneous (about 5 minutes). After the triclosan was completely dissolved, as evidenced by the absence of undissolved solid material, the sodium xylene sulfonate was added to the solution. The resulting mixture then was stirred to completely dissolve the sodium xylene sulfonate (about 5 minutes). Finally, the ammonium lauryl sulfate and water were added to the resulting solution, and the composition was stirred until homogeneous (about 5 minutes).

The composition had a weight ratio of surfactant:triclosan of 2.5:1, and was at least about 90% saturated with triclosan. The composition was evaluated for antibacterial efficacy against $S.$ $aureus$ and $E.$ $coli$ using a time kill test. Against $S.$ $aureus,$ the composition exhibited a log reduction of >4.07 in 30 seconds, while against $E.$ $coli$ the composition exhibited a log reduction of 3.90 in 30 seconds. Thus, the composition exhibited an excellent broad spectrum antibacterial activity. Also, the composition was an excellent hand wash composition in an actual use test, providing both good cleansing and a smooth feel to the hands.

EXAMPLE 15

Body Splash Composition

A composition in accordance with the present invention, suitable for use as a body splash, is prepared using the following ingredients in the following weight percentages:

| Ingredient | Weight Percent |
| --- | --- |
| Triclosan | 0.3 |
| Alkyl Polyglycoside | 0.3 |
| Propylene Glycol | 14.4 |
| Sodium Xylene Sulfonate | 10.0 |
| Ethanol | 10.0 |
| Fragrance | 0.05 |
| Water | q.s. |

The composition is prepared by combining the triclosan, propylene glycol, fragrance, and ethanol, and admixing the components until all the triclosan is dissolved, as evidenced by the absence of undissolved solid material. The sodium xylene sulfonate then is added, and the resulting mixture is stirred until the sodium xylene sulfonate is completely dissolved. Finally, the alkyl polyglycoside and water are added, and the mixture again is stirred until homogeneous. The resulting composition forms an excellent and refreshing body splash that provides a desirable level of bacterial reduction on the skin of the user.

EXAMPLE 16

Mouthwash composition

A composition in accordance with the present invention, suitable for use as a mouthwash, is prepared using the following ingredients in the following weight percentages:

| Ingredient | Weight Percent |
| --- | --- |
| Triclosan | 0.3 |
| Alkyl Polyglycoside | 0.3 |
| Propylene Glycol | 14.4 |
| Sodium Xylene Sulfonate | 10.0 |
| Denatured alcohol | 10.0 |
| Oil of Wintergreen (flavor) | 0.05 |
| Water | q.s. |

The composition is prepared by combining the triclosan, propylene glycol, flavor, and denatured alcohol, and admixing the components by any conventional means until all the triclosan is dissolved, as evidenced by the absence of undissolved solid material. Then, the sodium xylene sulfonate is added, and the resulting mixture is stirred until the sodium xylene sulfonate is completely dissolved. Finally, the alkyl polyglycoside and water are added, and the mixture again is stirred until homogeneous. The resulting composition forms an excellent and refreshing mouthwash that provides a desirable level of bacterial reduction on the teeth, gums, and tongue of the user.

EXAMPLE 17

Wet Wipe Composition

A composition in accordance with the present invention, suitable for impregnating a nonwoven material for the preparation of a wet wipe article, was prepared using the following ingredients in the following weight percentages:

| Ingredient | Weight Percent |
| --- | --- |
| Triclosan | 0.3 |
| Ammonium Lauryl Sulfate | 0.75 |
| Dipropylene Glycol | 5.0 |
| Sodium Xylene Sulfonate | 15.0 |
| Water | q.s. |

The composition was prepared by combining the triclosan and dipropylene glycol, and admixing the components until all the triclosan was dissolved, as evidenced by the absence of undissolved solid material. The sodium xylene sulfonate then was added, and the resulting mixture was stirred until the sodium xylene sulfonate was completely dissolved. Finally, the ammonium lauryl sulfate and water were added, and the mixture was again stirred until homogeneous.

A piece of nonwoven cellulosic web material (i.e., a commercial paper towel) then was dipped by hand into the composition to form a wet wipe article, suitable for wiping and cleaning surfaces, for example, hands. The article formed an excellent wet wipe and the impregnated antibacterial composition was freely expressed from the web to provide a broad spectrum antibacterial activity.

EXAMPLE 18

Hand Wash Composition

A composition in accordance with the present invention, suitable for use as a hand wash, was prepared. The composition comprised the following components at the indicated weight percentages:

| Ingredient | Weight Percent |
| --- | --- |
| Triclosan | 0.3 |
| Ammonium Lauryl Sulfate | 0.75 |
| Dipropylene Glycol | 5.0 |
| Sodium Xylene Sulfonate | 15.0 |
| Water | q.s. |

The composition was prepared by first admixing the triclosan and dipropylene glycol until homogeneous (about 5 minutes). After the triclosan was completely dissolved, as evidenced by the absence of undissolved solid material, the sodium xylene sulfonate was added to the solution. The mixture then was stirred to completely dissolve the sodium xylene sulfonate (about 5 minutes). Finally, the ammonium lauryl sulfate and water were added to the resulting solution, and the composition was stirred until homogeneous (about 5 minutes).

The composition had a weight ratio of surfactant:triclosan of 2.5:1 and was at least about 90% saturated with triclosan. The composition was evaluated for its antibacterial efficacy against *S. aureus, E. coli, K. pneum.,* and *S. choler.* using a time kill test, and a contact time of 30 seconds. The composition exhibited log reductions of >3.59, >4.49, >3.20, and >4.27 against the four test organisms, respectively.

Thus, the composition exhibited an excellent broad spectrum antibacterial activity. In addition, the composition was an excellent hand wash composition in an actual use test, providing both good cleansing and a smooth feel to the hands.

EXAMPLE 19

Comparison to a Previously Disclosed Composition

This example compares the antibacterial efficacy of a composition of the present invention to a previously disclosed composition. Accordingly, the composition of Example 18 was compared to the sole example disclosed in WO 98/01110. In both compositions, the active antibacterial agent was triclosan (TCS). Both compositions were evaluated for antibacterial efficacy in a time kill test against *S. aureus, E. coli, K. pneum.,* and *S. choler.* The example of WO 98/01110 was tested at 50% dilution, in accordance with the test procedure for viscous compositions. The following data summarizes the percent of active antibacterial agent in each composition at the test dilution (i.e., test dilution is 100% for the composition of Example 18 and 50% for the example of WO 98/01110), and the log reduction observed in the time kill test at a contact time of 30 seconds.

| | | Log Reduction at 30 seconds | | | |
| --- | --- | --- | --- | --- | --- |
| Composition | % TCS | *S. aureus* | *E. coli* | *K. pneum.* | *S. choler* |
| Example 18 | 0.3 | >4.60 | >4.50 | 4.21 | >4.68 |
| WO 98/01110 | 0.5 | 3.29 | 0.29 | 1.00 | 0.45 |

This example demonstrates the superior time kill performance of a composition of the present invention compared to a prior composition, especially against Gram negative bacteria. This superiority is demonstrated even through the comparative composition contained substantially more active antibacterial agent compared to the inventive composition. Thus, an inventive composition utilizes the active agent more efficiently, as illustrated in a higher log reduction using a reduced concentration of antibacterial agent.

EXAMPLE 20

Comparison to a Previously Disclosed Composition

This example compares the antibacterial efficacy of a composition of the present invention to a previously disclosed composition. Accordingly, the composition of Example 18 was compared to a composition disclosed in WO 96/06152. WO 96/06152 discloses effective compositions comprising TCS, an anionic surfactant, a hydrotrope, a hydric solvent, and further comprising an organic acid, specifically citric acid. WO 96/06152 contains additional pH adjusting agents, such as monoethanolamine and sodium hydroxide. Further, the examples disclosed in WO 96/06152 all have a pH of 4 or 9.1, with no examples having a desirable, neutral pH of about 7. A pH of about 7 is desired for compositions contacting skin or inanimate surfaces because compositions of pH substantially different from 7, such as 4 or 9.1, have a greater potential to damage the surfaces they contact. Accordingly, the composition of Example 1 of WO 96/06152 (hereafter referred to as composition 20-A) was prepared. For comparison, composition 20-A was prepared as above, except that the pH was adjusted to 7 by the addition of further monoethanolamine (this composition hereafter referred to as composition 20-B). To provide an additional comparison, the composition of Example 3 of WO 96/06152 was prepared, except that it was prepared at a pH of 7 by the addition of further monoethanolamine (this composition is hereafter referred to as composition 20-C). The table below summarizes the results of a time kill test on the compositions of this example against the bacteria indicated at a contact time of 30 seconds.

|  |  |  | Log Reduction at 30 Seconds | | | |
|---|---|---|---|---|---|---|
| Composition | pH | % TCS | S. aureus | E. coli | K. pneum. | S. choler. |
| Example 18 | 7.1 | 0.3 | >4.54 | >4.25 | 3.67 | >4.77 |
| Comparative 20-A | 4 | 0.075 | — | — | >4.84 | — |
| Comparative 20-B | 7 | 0.075 | — | — | 0.07 | — |
| Comparative 20-C | 7 | 0.15 | 4.44 | 2.91 | 0.28 | 4.67 |

This example demonstrates the superior time kill performance of a composition of the present invention compared to prior compositions, especially with respect to Gram negative bacteria at a pH of about 7. From the data presented in this example, it can be concluded that the compositions of WO 96/06152 rely substantially on a relatively extreme pH (either 4 or 9, as disclosed) to achieve a desirable, rapid and broad spectrum reduction of bacterial populations. This is in contrast to Example 18 of the present invention, which provides a rapid broad spectrum bacteria kill at the desirable pH of about 7.

EXAMPLE 21

Antibacterial Composition Containing PCMX

An antibacterial composition in accordance with the present invention containing p-chloro-m-xylenol (PCMX) as the active antibacterial agent was prepared. The composition contained the following components in the indicated weight percentages:

| Ingredient | Weight Percent |
|---|---|
| PCMX | 0.1 |
| Ethanol | 13.42 |
| Water | q.s. |

The composition was prepared by first mixing the PCMX and ethanol to completely solubilize the PCMX (about 5 minutes). After the PCMX was completely dissolved, as evidenced by the absence of undissolved solid material, the water was added, and the composition was stirred until homogeneous (about 5 minutes).

The composition was at least about 90% saturated with PCMX. The composition was evaluated for antibacterial efficacy against S. aureus, E. coli, K. pneum., and S. choler. using a time kill test. Against S. aureus, the composition exhibited a log reduction of 4.16 in 30 seconds; against E. coli the composition exhibited a log reduction of >4.34 in 30 seconds; against K. pneum. the composition exhibited a log reduction of 3.99 in 30 seconds; and against S. choler. the composition exhibited a log reduction of >4.04 in 30 seconds. Thus, the composition exhibited an excellent broad spectrum antibacterial activity.

EXAMPLE 22

Antibacterial Composition Containing PCMX

A composition in accordance with the present invention incorporating p-chloro-m-xylene as the active antibacterial ingredient was prepared. The composition contained the following components in the indicated weight percentages:

| Ingredient | Weight Percent |
|---|---|
| PCMX | 0.3 |
| Ammonium Lauryl Sulfate | 0.8 |
| Water | q.s. |

The composition was prepared by first combining the PCMX and water, then adding the ammonium lauryl sulfate and mixing the components for such time as to completely admix the components and dissolve the PCMX (about 2 hours).

The composition was at least about 90% saturated with PCMX. The composition was evaluated for its antibacterial efficacy against S. aureus and E. coli using a time kill test. Against S. aureus, the composition exhibited a log reduction of >3.57 in 30 seconds; and against E. coli the composition exhibited a log reduction of >4.17 in 30 seconds. Thus, the composition exhibited an excellent broad spectrum antibacterial activity.

Obviously, many modifications and variations of the invention as hereinbefore set forth can be made without departing from the spirit and scope thereof, and, therefore, only such limitations should be imposed as are indicated by the appended claims.

What is claimed is:

1. An antibacterial composition comprising:
   (a) about 0.001% to about 5%, by weight, of a phenolic antimicrobial agent;
   (b) about 0.1% to about 15%, by weight, of a surfactant selected from the group consisting of an anionic surfactant, a cationic surfactant, a nonionic surfactant, an ampholytic surfactant, and mixtures thereof;
   (c) 2% to about 30%, by weight, of a hydrotrope;
   (d) 2% to about 25%, by weight, of a water-soluble hydric solvent; and
   (e) water,
wherein the antimicrobial agent is present in an amount of at least 40% of saturation concentration, when measured at room temperature.

2. The composition of claim 1 comprising about 0.05% to about 2% by weight, of the phenolic antibacterial agent.

3. The composition of claim 1 wherein the phenolic antibacterial agent is selected from the group consisting of:
   (a) a 2-hydroxydiphenyl compound having the structure

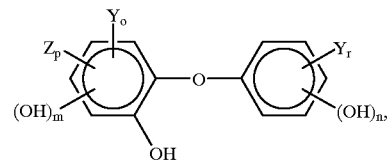

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1;

(b) a phenol derivative having the structure

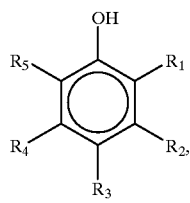

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl, and $R_5$ is hydro or nitro;

(c) a diphenyl compound having the structure

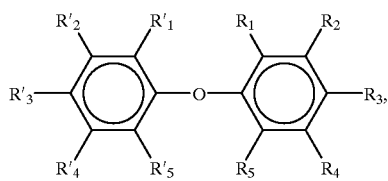

wherein X is sulfur or a methylene group, $R_1$ and $R'_1$ are hydroxy, and $R_2$, $R'_1$, $R_3$, $R'_3$, $R_4$, $R'_4$, $R_5$, and $R'_5$, independent of one another, are hydro or halo; and (d) mixtures thereof.

4. The composition of claim 3 wherein the antibacterial agent comprises triclosan, p-chloro-m-xylenol, or mixtures thereof.

5. The composition of claim 1 wherein the surfactant has a cation selected from the group consisting of sodium, ammonium, potassium, alkyl($C_{1-4}$) ammonium, dialkyl ($C_{1-4}$) ammonium, trialkyl ($C_{1-4}$)ammonium, alkanol($C_{1-4}$) ammonium, dialkanol($C_{1-4}$)ammonium, trialkanol($C_{1-4}$) ammonium, and mixtures thereof.

6. The composition of claim 1 wherein the surfactant is selected from the group consisting of a $C_8$–$C_{18}$ alkyl sulfate, a $C_8C_{18}$ alkamine oxide, and mixtures thereof.

7. The composition of claim 1 wherein the surfactant comprises a lauryl sulfate, an octyl sulfate, a 2-ethylhexyl sulfate, lauramine oxide, and mixtures thereof.

8. The composition of claim 1 having a pH of about 6 to about 8.

9. The composition of claim 1 having a log reduction against Gram positive bacteria of at least 2 after 30 seconds of contact, as measured against S. aureus, and a log reduction against Gram negative bacteria of at least 2.5 after 30 seconds of contact, as measured against E. coli.

10. The composition of claim 1 wherein the antibacterial agent is present in an amount of at least 50% of saturation concentration.

11. The composition of claim 1 wherein the antibacterial agent is present in an amount of at least 75% of saturation concentration.

12. The composition of claim 1 wherein the antibacterial agent is present in an amount of at least 95% of saturation concentration.

13. The composition of claim 1 wherein the surfactant comprises an anionic surfactant.

14. The composition of claim 1 wherein the surfactant comprises an ampholytic surfactant.

15. The composition of claim 1 wherein the hydrotrope is present in an amount of about 5% to about 20% by weight.

16. The composition of claim 1 wherein the hydric solvent present in an amount of about 5% to about 15% by weight.

17. The composition of claim 1 wherein the hydric solvent comprises an alcohol, a diol, a triol, and mixtures thereof.

18. The composition of claim 1 wherein the hydric solvent comprises methanol, ethanol, isopropyl alcohol, n-butanol, n-propyl alcohol, ethylene glycol, propylene glycol, glycerol, diethylene glycol, dipropylene glycol, tripropylene glycol, hexylene glycol, butylene glycol, 1,2,6-hexanetriol, sorbitol, PEG-4, or mixtures thereof.

19. The composition of claim 1 wherein the hydrotrope is selected from the group consisting of sodium cumene sulfonate, ammonium cumene sulfonate, ammonium xylene sulfonate, potassium toluene sulfonate, sodium toluene sulfonate, sodium xylene sulfonate, toluene sulfonic acid, xylene sulfonic acid, sodium polynaphthalene sulfonate, sodium polystyrene sulfonate, sodium methyl naphthalene sulfonate, disodium succinate, and mixtures thereof.

20. The composition of claim 1 having a pH of about 5 to about 8.

21. The composition of claim 1 comprising:
(a) about 0.01% to about 0.5%, by weight, of the antimicrobial agent;
(b) about 0.1% to about 5%, by weight, of the surfactant;
(c) about 5% to about 20%, by weight, of the hydrotrope; and
(d) about 2% to about 15%, by weight, of the hydric solvent.

22. The composition of claim 21 having a pH of about 6 to about 8.

23. An antibacterial composition comprising:
(a) about 0–0.001% to about 5%, by weight, of a phenolic antimicrobial agent;
(b) about 0.1% to about 15%, by weight, of a surfactant selected from the group consisting of an anionic surfactant, a cationic surfactant, a nonionic surfactant, an ampholytic surfactant, and mixtures thereof;
(c) about 2% to about 30%, by weight, of a hydrotrope;
(d) about 2% to about 25%, by weight, of a water-soluble hydric solvent; and
(e) water,
wherein the composition has a log reduction against Gram positive bacteria of at least 2 after 30 seconds of contact, as measured against S. aureus, and has a log reduction against Gram negative bacteria of at least 2.5 after 30 seconds of contact, as measured against E. coli.

24. The composition of claim 1 wherein the antibacterial agent is present in an amount of at least 50% of saturation concentration.

25. The composition of claim 23 wherein the antibacterial agent is present in an amount of at least 75% of saturation concentration.

26. The composition of claim 23 wherein the antibacterial agent is present in an amount of at least 95% of saturation concentration.

27. A method of reducing a bacteria population on a surface comprising contacting the surface with a composition of claim 1 for 30 seconds to achieve a log reduction of at least 2 against S. aureus and a log reduction of at least 2.5 against E. coli, then rinsing the composition from the surface.

28. The method of claim 27 wherein the composition contacts the surface for 60 seconds to achieve a log reduction of at least 3 against S. aureus.

29. The method of claim 27 wherein the composition contacts the surface for 60 seconds to achieve a log reduction of at least 3.75 against *E. coli.*

30. The method of claim 27 wherein the composition contacts the surface for 30 seconds to achieve a log reduction of at least 2 against *K. pneum.*

31. The method of claim 27 wherein the surface is a skin of a mammal.

32. The method of claim 27 wherein the surface is a hard, inanimate surface.

33. A method of reducing a bacteria population on a surface comprising contacting the surface with a composition of claim 23 for 30 seconds to achieve a log reduction of at least 2 against *S. aureus* and a log reduction of at least 2.5 against *E. coli,* then rinsing the composition from the surface.

34. The method of claim 33 wherein the composition contacts the surface for 60 seconds to achieve a log reduction of at least 3 against *S. aureus.*

35. The method of claim 33 wherein the composition contacts the surface for 60 seconds to achieve a log reduction of at least 3.75 against *E. coli.*

36. The method of claim 33 wherein the composition contacts the surface for 30 seconds to achieve a log reduction of at least 2 against *K. pneum.*

* * * * *

UNITED STATES PATENT AND TRADEMARK OFFICE
CERTIFICATE OF CORRECTION

PATENT NO.   : 6,107,261
DATED        : August 22, 2000
INVENTOR(S)  : Timothy J. Taylor et al.

It is certified that error appears in the above-identified patent and that said Letters Patent is hereby corrected as shown below:

Column 45,
Line 22, replace "O" (in the center of the diagram) with "X".
Line 30, replace "$R_2, R'_1, R_3$" with "$R_2, R'_2, R_3$".
Line 44, replace "$C_8C_{18}$" with "$C_8$-$C_{18}$".

Column 46,
Line 35, replace "0-0.001%" with "0.001%".

Signed and Sealed this

Seventh Day of August, 2001

*Attest:*

NICHOLAS P. GODICI
*Attesting Officer*   Acting Director of the United States Patent and Trademark Office